(12) United States Patent
Nakano et al.

(10) Patent No.: US 8,404,617 B2
(45) Date of Patent: Mar. 26, 2013

(54) PHOTOCATALYST MATERIAL, PHOTOCATALYST COMPOSITION USING THE SAME AND PHOTOCATALYST PRODUCT

(75) Inventors: Kayo Nakano, Yokohama (JP); Akira Sato, Yokohama (JP); Yasuhiro Shirakawa, Yokohama (JP); Masami Okamura, Yokohama (JP); Ryotaro Matsuda, Yokosuka (JP); Takaya Kamakura, Yokosuka (JP); Kazunari Otsuka, Yokohama (JP); Kiyoshi Yokokura, Yokosuka (JP); Hideki Okawa, Yokohama (JP); Ariyoshi Ishizaki, Yokohama (JP)

(73) Assignee: Toshiba Materials Co., Ltd., Yokohama-shi (JP)

( * ) Notice: Subject to any disclaimer, the term of this patent is extended or adjusted under 35 U.S.C. 154(b) by 54 days.

(21) Appl. No.: 12/184,611

(22) Filed: Aug. 1, 2008

(65) Prior Publication Data

US 2009/0023583 A1    Jan. 22, 2009

Related U.S. Application Data

(63) Continuation of application No. PCT/JP2007/051600, filed on Jan. 31, 2007.

(30) Foreign Application Priority Data

Feb. 1, 2006  (JP) ................. 2006-024918
May 31, 2006 (JP) ................. 2006-152685
Dec. 28, 2006 (JP) ................. 2006-354990

(51) Int. Cl.
    *B01J 23/30*       (2006.01)
(52) U.S. Cl. ...................................... 502/305
(58) Field of Classification Search ................. None
    See application file for complete search history.

(56) References Cited

U.S. PATENT DOCUMENTS 5,616,532 A    4/1997  Heller et al.
(Continued)

FOREIGN PATENT DOCUMENTS

EP    1 857 179 A1    11/2007
JP      4-42057        7/1992
(Continued)

OTHER PUBLICATIONS

Yanagisawa, T, , Changes in Properties of GaN Blue Light Emitting Diodes over Time, May 28, 1986, Electronics Letters, vol. 22 No. 16, pp. 846-847.*

(Continued)

*Primary Examiner* — Melvin C Mayes
*Assistant Examiner* — Stefanie Cohen
(74) *Attorney, Agent, or Firm* — Oblon, Spivak, McClelland, Maier & Neustadt, L.L.P.

(57) ABSTRACT

An object of the invention is to provide a photocatalyst material having a higher catalyst effect than conventional photocatalyst materials. The photocatalyst material of the invention contains, as its major component, a tungsten oxide powder excited by a light source which emits light having a wavelength of 430 to 500 nm, the photocatalyst material having a decomposition ability of 50% or more wherein the decomposition ability is given by the following equation based on the following test: [Test for decomposition ability]: 1 g of a tungsten oxide powder and 20 ppm of acetaldehyde (amount A) are poured into a 3-liter glass container, and acetaldehyde (amount B) is measured after light having a peak wavelength of 460 nm±10 nm is irradiated to the mixture for 2 hours to measure the decomposition ability (%): Decomposition ability (%)=[(acetaldehyde amount A−acetaldehyde amount B)/acetaldehyde amount A]×100.

18 Claims, 17 Drawing Sheets

U.S. PATENT DOCUMENTS

| | | | | |
|---|---|---|---|---|
| 5,854,169 | A | * | 12/1998 | Heller et al. .................. 502/242 |
| 2004/0024108 | A1 | * | 2/2004 | Sugihara ........................ 524/497 |
| 2005/0025700 | A1 | * | 2/2005 | Bulian et al. .................. 423/606 |
| 2005/0227008 | A1 | * | 10/2005 | Okada et al. ............... 427/372.2 |

FOREIGN PATENT DOCUMENTS

| | | |
|---|---|---|
| JP | 2001-70800 | 3/2001 |
| JP | 2001-152130 | 6/2001 |
| JP | 2001-276194 | 10/2001 |
| JP | 2002-293544 | 10/2002 |
| JP | 2002-346394 | 12/2002 |
| JP | 2006-198464 | 8/2006 |
| SU | 1092895 A | 6/1985 |

OTHER PUBLICATIONS

Kominami, Hiroshi et al, Synthesis of highly active ungsten oxide photocatalysts for oxygen evolution by hydrothermal treatment of aqueous tungstic acid solutions, Oct. 25, 2001, Journal of Material Chemistry, vol. 11, p. 3222-3227.*

Ashokkumar et al, preperation and characterization of doped WO3 photocatalyst powders, journal of materials science letter, 24, 1989, pp. 21352139.*

Baeck et al, enhancement of photocatalytic and electrochromic properties of electrochemically fabricated mesoporous WO3 thin films, 2003, adv. mater. 15, No. 15, pp. 1269-1273.*

Kominami H. et al., "Solvothermal syntheses of semiconductor photocatalysts of ultra-high actvities", Catalysis Today, 2003, vol. 84, No. 3/4, p. 181-189.

Bamwenda G.R. et al., "The visible light induced photocatalytic activity of tungsten trioxide powders", Applied Catalysis A: General 2001, vol. 210, p. 181-191.

Ashokkumar M. et al., "Preparation and characterization of doped $WO_3$ photocatalyst powders" Journal of Materials Science, 1989, vol. 24, No. 6, p. 2135-2139.

Extended European Search Report issued May 20, 2011, in Application No. / Patent No. 07707786.5-1270 / 1980320 PCT/JP2007051600.

M. Ashokkumar, et al., "Factors influencing the Photocatalytic Efficiency of WO3 Particles", Journal of Photochemistry and Photobiology , A: Chemistry, vol. 49, No. 1-2, Elsevier, XP026685608, Sep. 1989, pp. 249-258.

Office Action issued Jan. 25, 2011, in Japan Patent Application No. 2006-354990 (with English translation).

Search Report issued May 15, 2012 in European Patent Application No. 07 707 786.5-1270.

Urša Opara Krašovec, et al. "Preparation and Characterisation of Nano-Structured $WO_3$-$TiO_2$ Layers for Photoelectrochromic Devices", Journal of Sol-Gel Science and Technology, XP019213047, vol. 36, No. 1, Oct. 1, 2005, pp. 45-52.

* cited by examiner

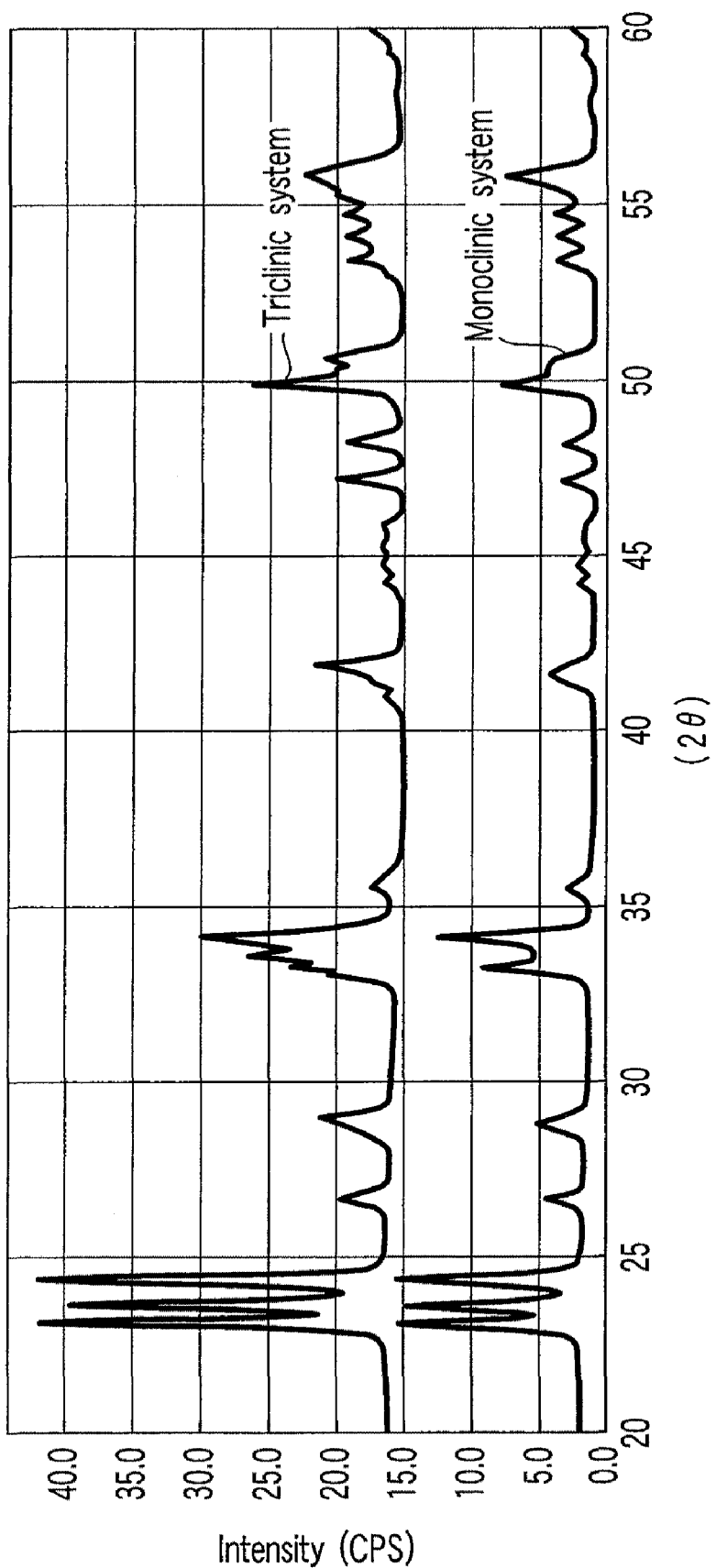
F I G. 4

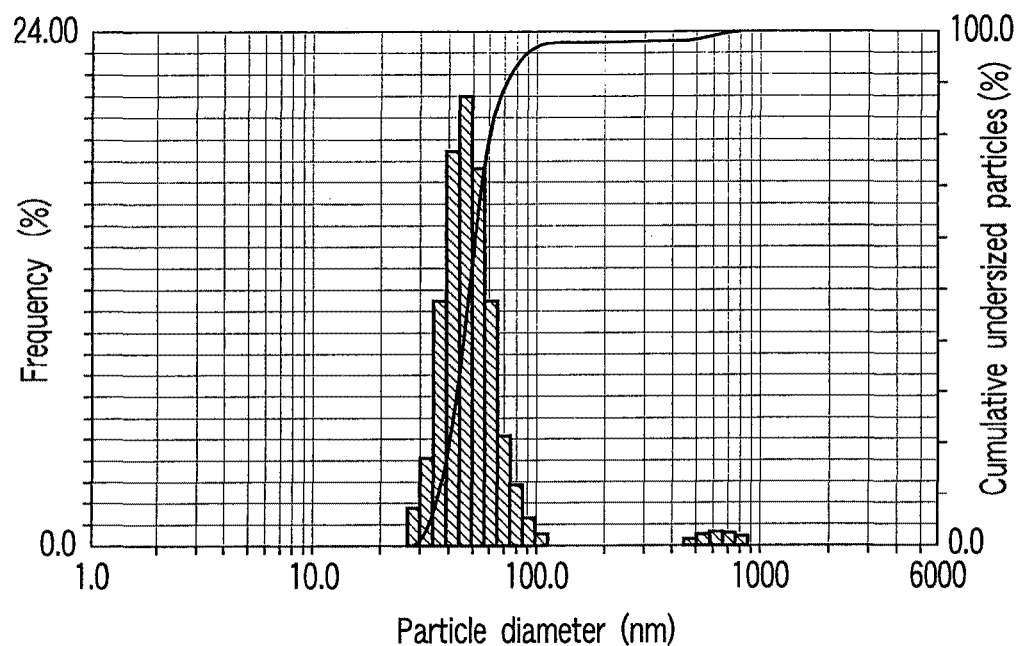
F I G. 8
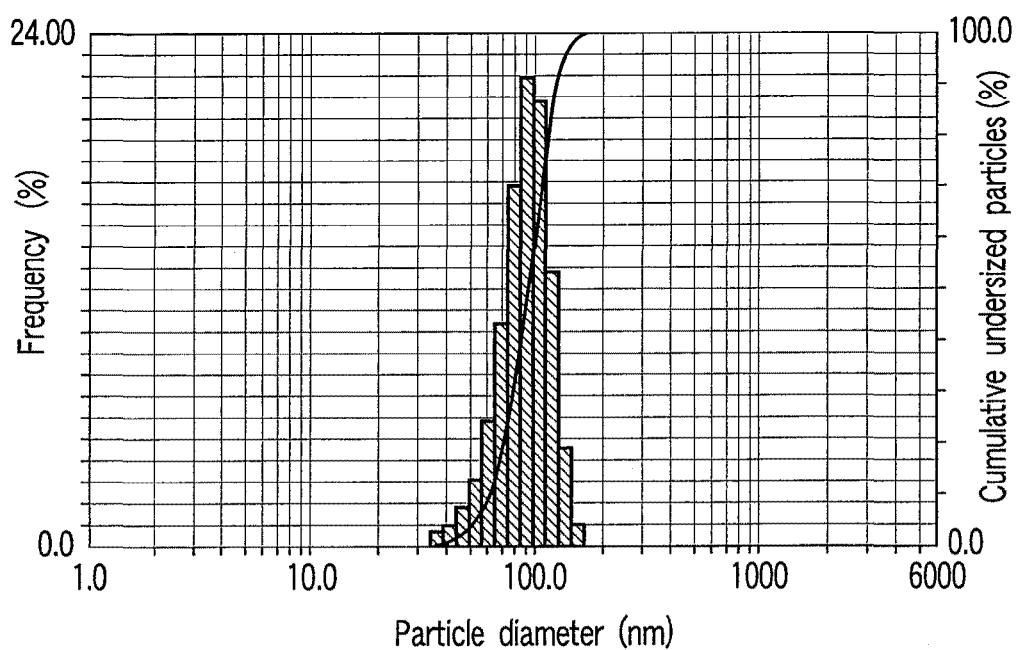
F I G. 9

400nm

200nm

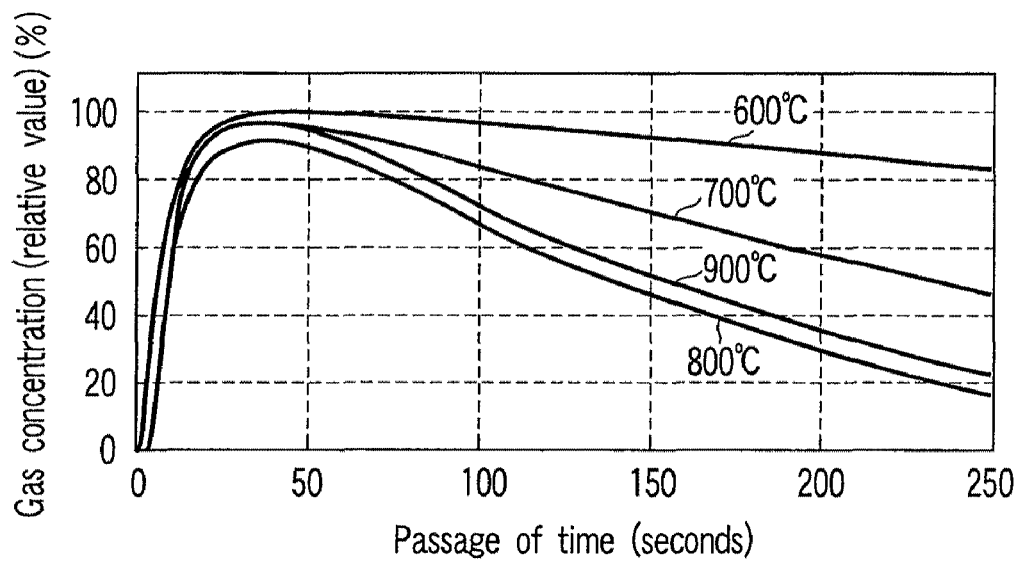
F I G. 12
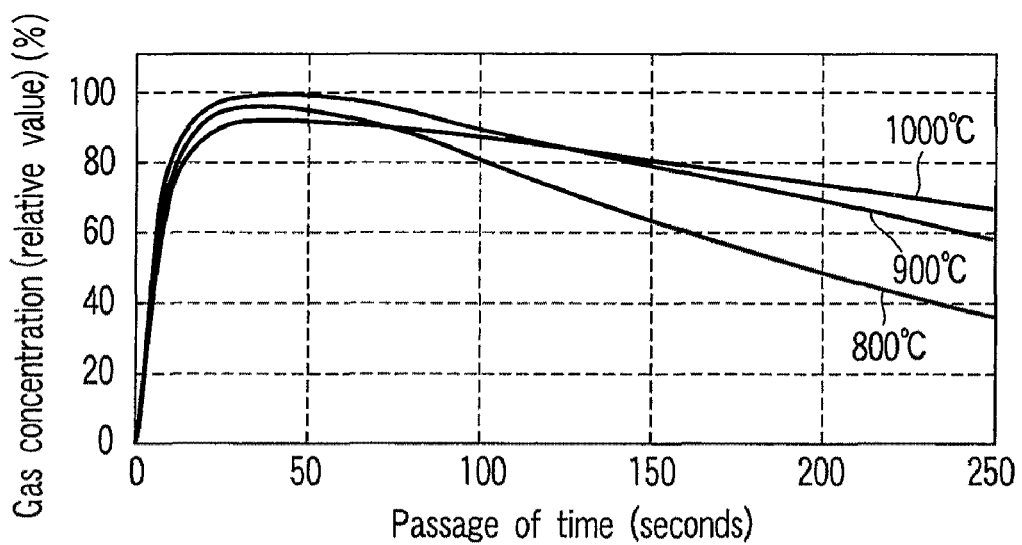
F I G. 13

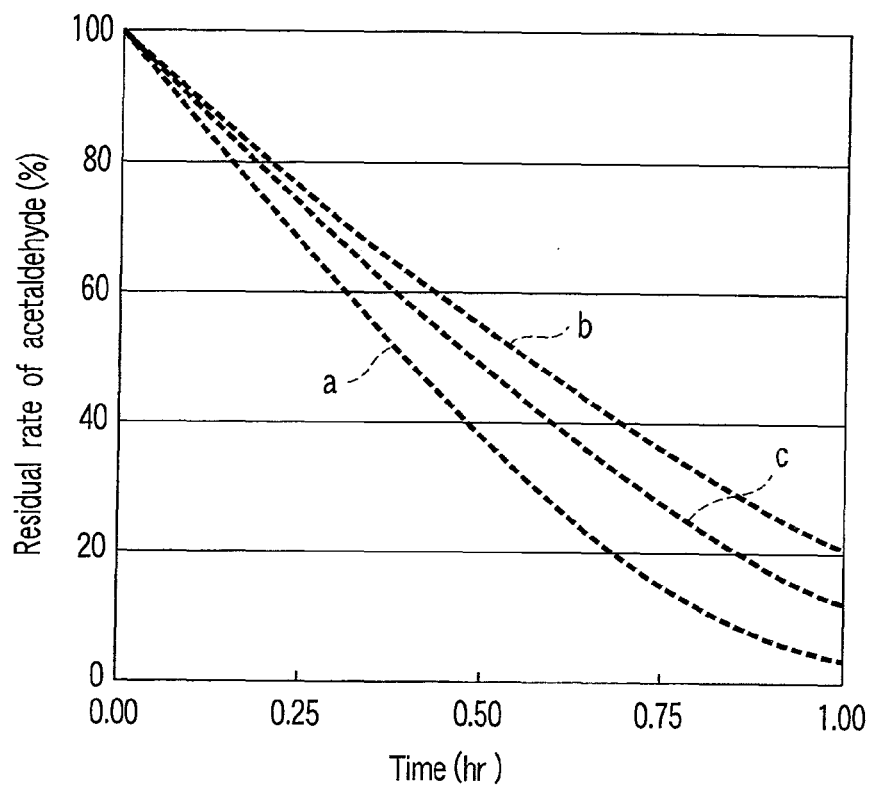
F I G. 18
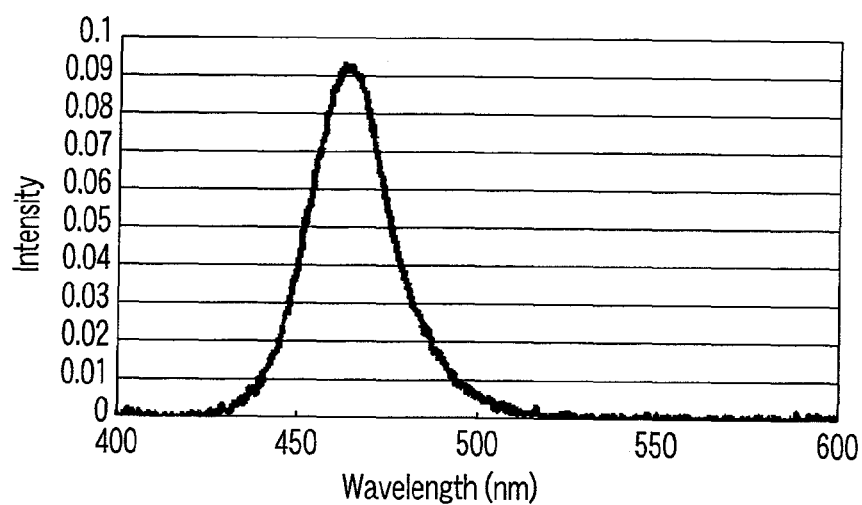
F I G. 19

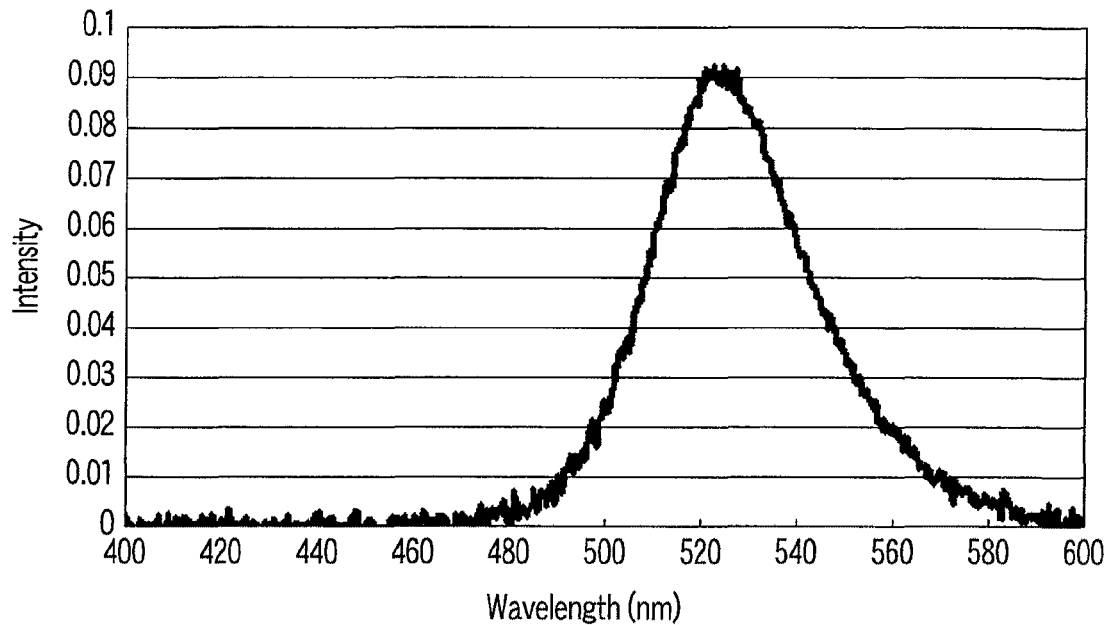
F I G. 20
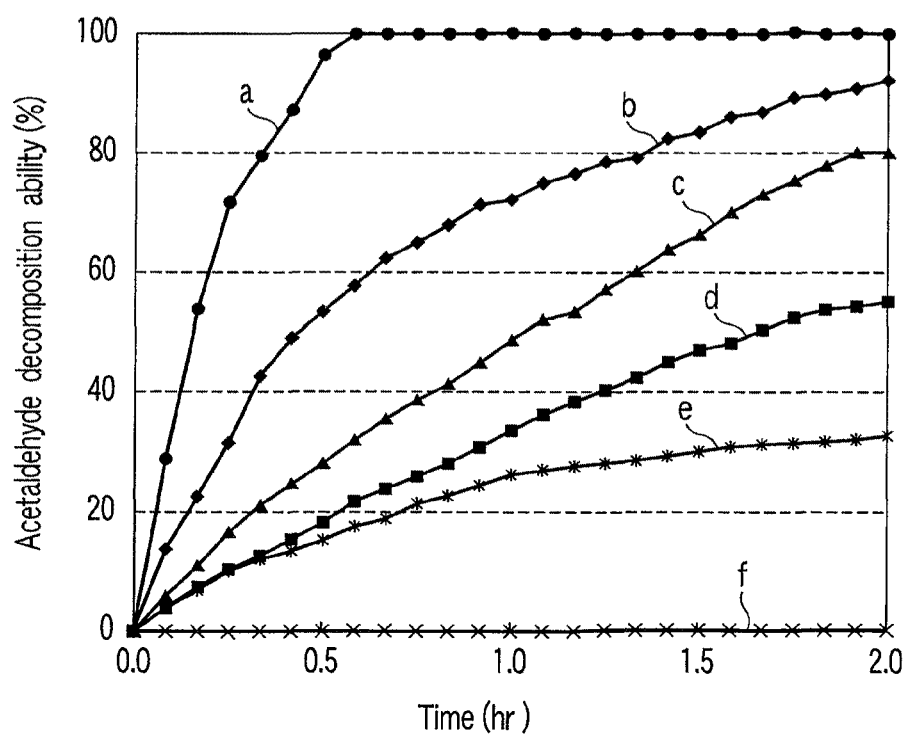
F I G. 21

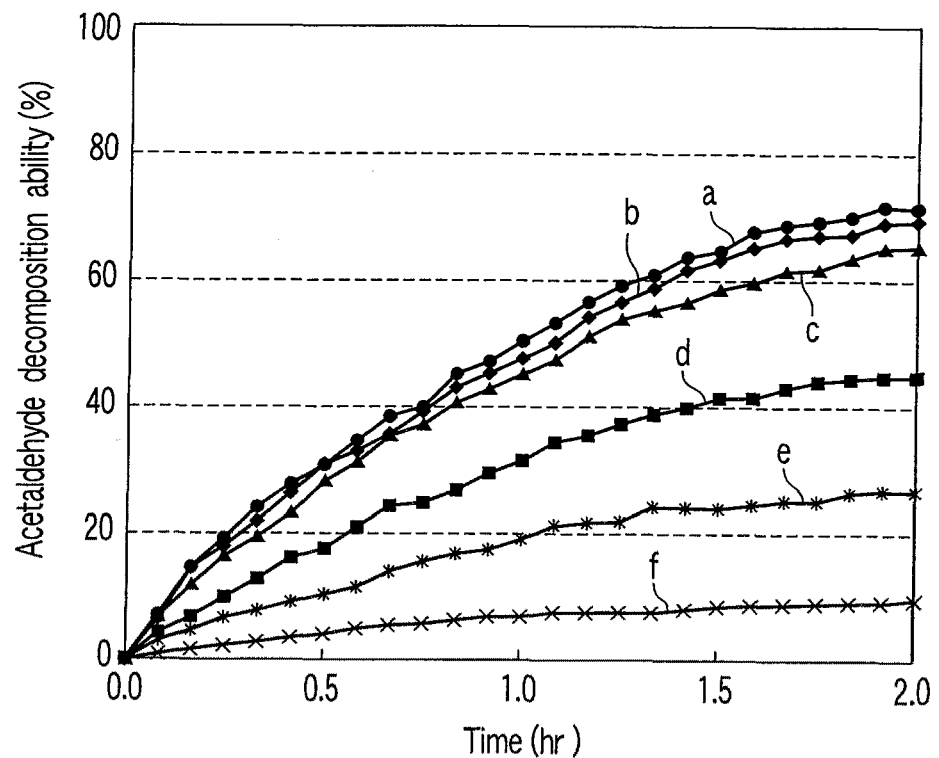
F I G. 22
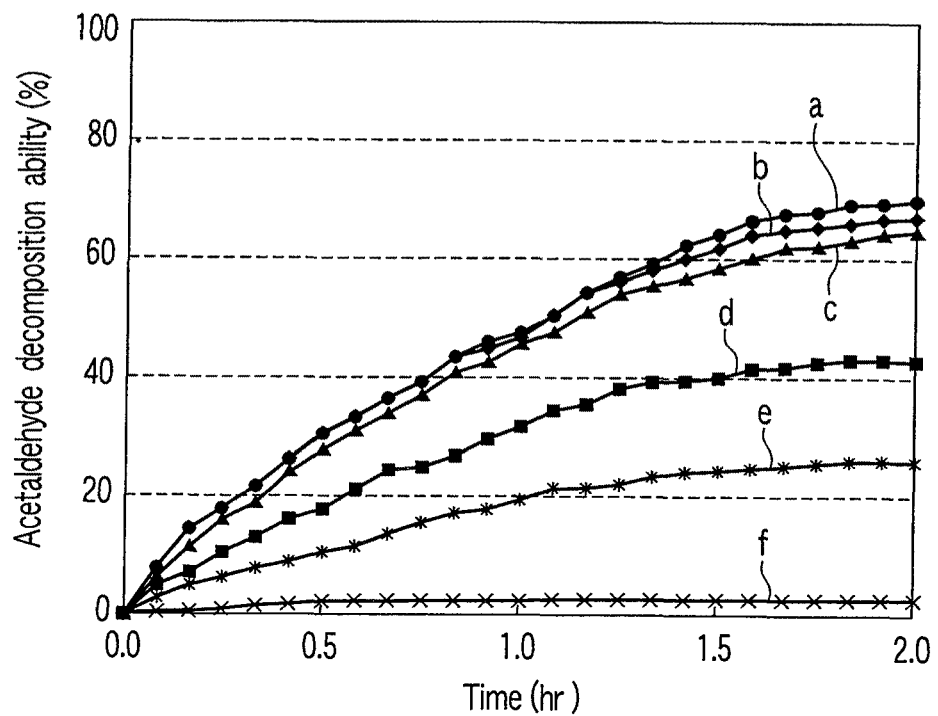
F I G. 23

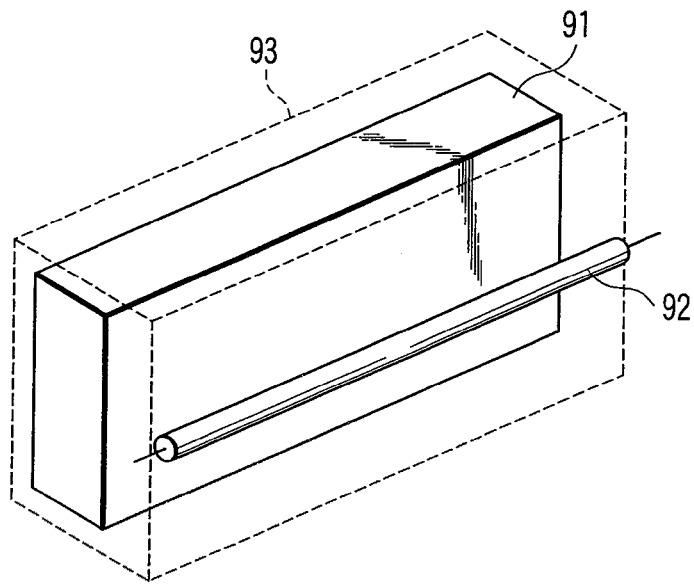
F I G. 26
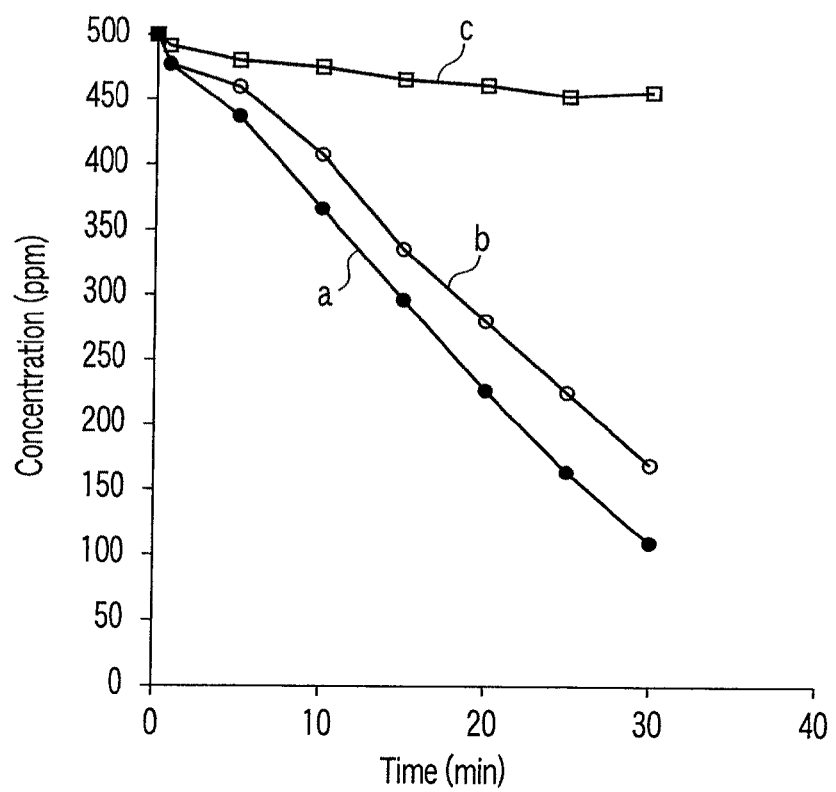
F I G. 27

PHOTOCATALYST MATERIAL, PHOTOCATALYST COMPOSITION USING THE SAME AND PHOTOCATALYST PRODUCT

CROSS REFERENCE TO RELATED APPLICATIONS

This is a Continuation Application of PCT Application No. PCT/JP2007/051600, filed Jan. 31, 2007, which was published under PCT Article 21(2) in Japanese.

CROSS-REFERENCE TO RELATED APPLICATIONS

This application is based upon and claims the benefit of priority from prior Japanese Patent Applications No. 2006-024918, filed Feb. 1, 2006; No. 2006-152685, filed May 31, 2006; and No. 2006-354990, filed Dec. 28, 2006, the entire contents of all of which are incorporated herein by reference.

BACKGROUND OF THE INVENTION

1. Field of the Invention

The present invention relates to a photocatalyst material, a photocatalyst composition and a photocatalyst product.

2. Description of the Related Art

As is well known, when a photocatalyst material is irradiated with light having an energy larger than the bandgap thereof, electrons appear in the conductive band and holes appear in the valence band by photoexcitation. As a consequence, these electrons and holes are diffused to the surface of the powder and brought into contact with oxygen and moisture, with the result that these electrons are adsorbed and reduced to produce super oxide anions. The holes, on the other hand, oxidize moisture to form hydroxy radicals. These products resultantly exhibit sterilizing force, organic decomposability and hydrophilic ability through their redox reactions.

Here, examples of the "light having an energy larger than the bandgap" include ultraviolet rays and visible light. As the "light source", sunlight, various lamps and light-emitting diodes are used.

As the photocatalyst materials, a titanium oxide ($TiO_2$) powder has been primarily used so far. However, when it is intended to obtain the bandgap energy (wavelength of 380 nm or less) of a titanium oxide powder by sunlight, only about 2% of the light can be utilized. In view of this, much attention has been recently focused on tungsten oxide ($WO_3$), instead of a titanium oxide powder, as photocatalyst materials capable of utilizing visible light region (400 to 800 nm) which is a major wavelength of sunlight.

For example, Patent Document 1 describes that a tungsten oxide film formed by a sputtering method is used as a photocatalyst. Here, even if the photocatalyst is a film, the effect of the photocatalyst is obtained. However, the photocatalyst having a film form is unsatisfactory to gain sufficient surface area and is therefore decreased in catalyst effect per unit volume. Also, because the sputtering method is a film-forming technology using vacuum, the equipment is large-scaled, leading to high cost. Moreover, the sputtering method has the problem that a film can be formed only on a highly heat-resistant material (base material) because the base material (material to be coated) is exposed to a high-temperature circumstance.

When the photocatalyst is made of a tungsten oxide powder, on the other hand, it has the following merits. Specifically, because the entire surface of the powder can be used as the catalyst surface, the catalyst effect per unit volume can be improved. Also, a method in which the powder is mixed with a resin and applied may be adopted and it is therefore unnecessary to expose the base material to a high-temperature circumstance and the powder can be applied to any place. In order to increase the catalyst surface per unit volume, the powder is preferably made into microparticles having an average particle diameter of 1 μm or less.

As the method used to obtain microparticles of a tungsten oxide powder, for example, Patent Document 2 is known. Examples of the method of heat-treating ammonium paratungstate (hereinafter, referred to as APT) in the air are given in this Patent Document, Paragraphs 0008 and 0009. This method succeeds in obtaining microparticles having a BET specific surface area of 3 to 5 $m^2/g$ and an average particle diameter of 0.2 to 0.3 μm when the specific gravity of tungsten oxide is 7.3.

In the meantime, examples of the light source used to excite a photocatalyst include, as mentioned above, sunlight, various light-emitting diodes and various lamps. Here, the photocatalyst is excited by a specified wavelength to develop its catalytic effect. Therefore, if the wavelength of the light source does not accord to the exciting wavelength of the photocatalyst, sufficient characteristics cannot be obtained. For example, Patent Document 3 for improving such a disadvantage is known. In Patent Document 3, a method is disclosed in which a light-emitting material is made to emit light having a wavelength different from that of a light source by mixing the photocatalyst with the light-emitting material (fluorescent body), to excite the photocatalyst by the light having that wavelength.

According to Patent Document 3, there is disclosed such a fact that even if a $TiO_2$ powder which is scarcely excited by the visible light is used, this powder exhibits the ability of decomposing formaldehyde under daylight color (under sunlight). However, the decomposing ability thereof is very poor. To mention in more detail, the method of Patent Document 3 takes 24 hours to decompose 50 ppm of formaldehyde.

On the other hand, much attention has been recently focused on tungsten oxide ($WO_3$) as photocatalyst materials which are used in the visible light region (400 to 800 nm) as mentioned above. According to this photocatalyst, a certain level of catalyst characteristics is, indeed, obtained in the visible light region.

Patent Document 1: Jpn. Pat. Appln. KOKAI Publication No. 2001-152130

Patent Document 2: Jpn. Pat. Appln. KOKAI Publication No. 2002-293544

Patent Document 3: Jpn. Pat. Appln. KOKAI Publication No. 2002-346394

Patent Document 4: Jpn. Pat. Appln. KOKOKU Publication No. 4-42057

BRIEF SUMMARY OF THE INVENTION

However, no satisfactory characteristic has been obtained yet. It is disclosed in Example 1 described in Patent Document 4 that a $WO_3$ powder is irradiated with light from a copying fluorescent lamp (ultraviolet ray output: 2.1 W, wavelength: 300 to 490 nm, major wavelength: 370 nm) to obtain the result that 90% of 10 ppm acetaldehyde is decomposed in 24 minutes. However, the $WO_3$ powder is required in an amount as much as 100 g. Such characteristics make it necessary to apply the $WO_3$ powder in a large amount to, for example, the place where a deodorizing operation is performed.

It is an object of the present invention to provide a photocatalyst material having a more excellent catalyst effect than conventional photocatalyst materials, a photocatalyst composition containing this photocatalyst material and a photocatalyst product using this photocatalyst material and enabling space saving and reduction in weight.

The above object can be attained by the following photocatalyst material, and the following photocatalyst composition and photocatalyst product using the photocatalyst material according to the present invention.

(1) There is provided a photocatalyst material comprising, as its major component, a tungsten oxide powder excited by a light source which emits light having a wavelength of 430 to 500 nm, the photocatalyst material having a decomposition ability of 50% or more wherein the decomposition ability is given by the following equation based on the following test:

[Test for Decomposition Ability]

1 g of a tungsten oxide powder and 20 ppm of acetaldehyde (amount A) are poured into a 3-liter glass container, and acetaldehyde (amount B) is measured after light having a peak wavelength of 460 nm±10 nm is irradiated to the mixture for 2 hours to measure the decomposition ability (%):

Decomposition ability (%)=[(acetaldehyde amount $A$−acetaldehyde amount $B$)/acetaldehyde amount $A$]×100.

(2) There is provided the photocatalyst material according to (1), wherein the light source is a light-emitting diode using a blue light-emitting semiconductor element.

(3) There is provided the photocatalyst material according to (1), wherein the light source is sunlight.

(4) There is provided the photocatalyst material according to (1), wherein the light source is a fluorescent lamp.

(5) There is provided the photocatalyst material according to (1), wherein dose of light having a wavelength of 430 to 500 nm is 1 mW/cm$^2$ or more.

(6) There is provided the photocatalyst material according to (1), wherein the decomposition ability is 90% or more and 100% or less.

(7) There is provided the photocatalyst material according to (1), containing a monoclinic system as its major phase.

(8) There is provided the photocatalyst material according to (1), having an average particle diameter of 10 μm or less.

(9) There is provided a photocatalyst composition containing the photocatalyst material according to (1) in an amount of 50% by mass or more.

(10) There is provided the photocatalyst composition according to (9), containing a titanium oxide powder in an amount less than 50% by mass.

(11) There is provided a photocatalyst product using the photocatalyst composition according to (9).

(12) There is provided the photocatalyst product according to (11), having a catalyst effect on at least one of an organic material, NO$_x$ and SO$_x$.

(13) There is provided the photocatalyst product according to (11) or (12), wherein the photocatalyst composition is bound with a surface of a base substrate by a binder.

(14) There is provided a photocatalyst material comprising, as its major component, a tungsten oxide microparticle excited by irradiation with visible light, the photocatalyst material having such a decomposition ability that a residual rate of acetaldehyde is 50% or less 30 minutes after 10 ppm of acetaldehyde gas is introduced into an airtight container having a capacity of 3 liters and 0.1 g of tungsten oxide microparticles in the container are irradiated with blue light.

(15) There is provided the photocatalyst material according to (14), wherein a light source which emits blue light is a GaN system light-emitting diode having a light-emitting peak in the vicinity of 470 nm.

(16) There is provided the photocatalyst material according to (14), containing a monoclinic system as its major phase.

(17) There is provided the photocatalyst material according to (14), having an average particle diameter of 10 μm or less.

(18) There is provided a photocatalyst composition containing the photocatalyst material according to (14) in an amount of 50% by mass or more.

(19) There is provided the photocatalyst composition according to (18), containing a titanium oxide powder in an amount less than 50% by mass.

(20) There is provided a photocatalyst product using the photocatalyst composition according to (18).

(21) There is provided the photocatalyst product according to (20), having a catalyst effect on at least one of an organic material, NO$_x$ and SO$_x$.

(22) There is provided the photocatalyst product according to (20) or (21), wherein the photocatalyst composition is bound with a surface of a base substrate by a binder.

The present invention can provide a photocatalyst material having a more excellent catalyst effect than conventional photocatalyst materials, a photocatalyst composition containing this photocatalyst material and a photocatalyst product using this photocatalyst material and enabling space saving and reduction in weight.

BRIEF DESCRIPTION OF THE SEVERAL VIEWS OF THE DRAWING

FIG. 4 shows one example of X-ray diffraction patterns of a triclinic system and a monoclinic system of tungsten trioxide (WO$_3$).

FIG. 8 is a graph showing the grain distribution (relation among particle diameter, frequency and cumulative undersized particles) after particles are dispersed.

FIG. 9 is a graph showing the grain distribution (relation among particle diameter, frequency and cumulative undersized particles) of a WO$_3$ dispersed paint.

FIG. 12 is a characteristic diagram showing the acetaldehyde decomposition ability of each tungsten trioxide photocatalyst microparticle when the baking temperature is varied to 600° C., 700° C., 800° C. and 900° C. in a fourth embodiment.

FIG. 13 is a characteristic diagram showing the acetaldehyde decomposition ability of each tungsten trioxide photocatalyst microparticle when the baking temperature is varied to 800° C., 900° C. and 1000° C. in the fourth embodiment.

FIG. 18 shows the relation between time and acetaldehyde residual rate of a lighting equipment in a seventh embodiment and a fluorescent lamp with a $TiO_2$ photocatalyst, a fluorescent lamp with a $TiO_2$ photocatalyst, and a lighting equipment with $TiO_2$ photocatalyst and a fluorescent lamp with a $TiO_2$ photocatalyst.

FIG. 19 shows one example of a blue peak wavelength of a blue light-emitting diode used in a test of the present invention.

FIG. 20 shows one example of a greenish blue peak wavelength of a greenish blue light-emitting diode used in a test of the present invention.

FIG. 21 shows a first decomposition ability test when samples 1 to 6 according to this embodiment are excited by a blue light-emitting diode.

FIG. 22 shows a first decomposition ability test when samples 1 to 6 according to this embodiment are excited by sunlight.

FIG. 23 shows a first decomposition ability test when samples 1 to 6 according to this embodiment are excited by a fluorescent lamp.

FIG. 26 shows an embodiment of a deodorizing apparatus according to this embodiment.

FIG. 27 shows the acetaldehyde decomposition ability of the deodorizing apparatus according to this embodiment.

DETAILED DESCRIPTION OF THE INVENTION

Figure 1A:
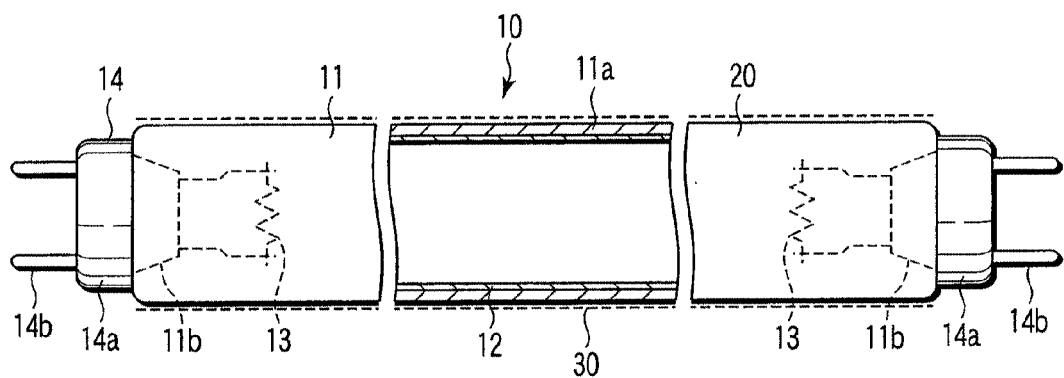
FIG. 1A is a sectional view including a broken section of a fluorescent lamp according to the present invention.
Figure 1B:
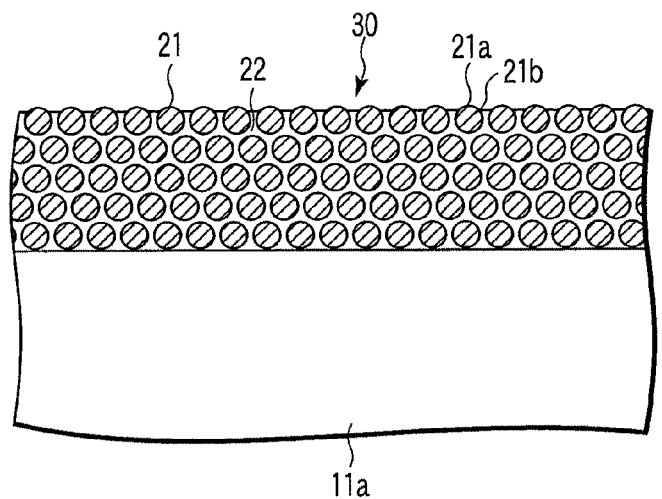
FIG. 1B is a typical sectional view of a photocatalyst film which is one structure of a fluorescent lamp according to the present invention.

An embodiment according to the invention will be explained with reference to the drawings.
[Structure of a Fluorescent Lamp]
FIGS. 1A and 1B are sectional views typically showing the structure of a fluorescent lamp according to the present invention. Specifically, FIG. 1A is a sectional view including a broken section and FIG. 1B is a typical sectional view of a photocatalyst film which is one structure of the above fluorescent lamp.

Reference numeral 10 in the figure represents a fluorescent lamp as a photocatalyst product. The fluorescent lamp 10 is constituted of a fluorescent lamp body 20 and a photocatalyst film 30 formed on the surface of this fluorescent lamp body 20. The above fluorescent lamp body 20 is constituted of a light-transmittable discharge container 11, a fluorescent body layer 12, a pair of electrodes 13, 13, a discharge medium (not shown) and a base 14.

The light-transmittable discharge container 11 is constituted of an elongate glass bulb 11a and a pair of flare stems 11b. The glass bulb 11a is made of soda lime glass. The flare stem 11b is provided with an exhaust pipe, a flare, an internal lead-in wire and an external lead-in wire. The exhaust pipe is used in such a manner that it is communicated with the inside and outside of the light transmittable discharge container 11 to exhaust the inside of the light transmittable discharge container 11 and to seal a discharge medium. Then, the exhaust pipe is sealed after the discharge medium is sealed. Both ends of the glass bulb 11a are sealed with the above flare to form the light transmittable discharge container 11. The base end of the internal lead-in wire is embedded inside the flare stem 11b air-tightly and connected with the external lead-in wire. The top of the external lead-in wire is embedded in the flare stem 11b and the base end thereof is led out of the light transmittable discharge container 11.

The fluorescent body layer 12 is constituted of a three-wavelength light-emitting fluorescent body and formed on the inside surface of the light transmittable discharge container 11. In the three-wavelength light-emitting fluorescent body, $BaMgAl_{16}O_{27}$:Eu is for blue light-emitting use, $LaPO_4$:Ce, Tb is for green light-emitting use and $Y_2O_3$:Eu is for red light-emitting use. The pair of electrodes 13, 13 is connected between the ends of a pair of internal lead-in wires disposed opposite to and apart from each other in each inside of both ends of the light transmittable discharge container 11. Also, the electrode 13 is constituted of a coil filament of tungsten and an electron-emitting material stuck to the coil filament.

The above discharge medium is constituted of mercury and argon and sealed inside the light transmittable discharge container 11. The mercury is sealed in a proper amount through the exhaust pipe. The argon is sealed in an amount of about 300 Pa. The base 14 is constituted of a base body 14a and a pair of base pins 14b, 14b. The base body 14a has a cap-form and is stuck to both ends of the light transmittable discharge container 11. The pair of base pins 14b, 14b is supported by the base body 14a in such a manner as to be insulated from the base body 14a and connected to each external lead-in wire.

The photocatalyst film 30 is a film made of a photocatalyst paint containing tungsten trioxide microparticles (average particle diameter: 0.1 μm) as its major component. The film thickness of the photocatalyst film 30 is about 0.5 to 3 μm. The tungsten trioxide microparticles have a monoclinic system crystal structure even after the coating is finished. The photocatalyst film 30 is formed of photocatalyst microparticles 21 and a binder 22, such as alumina microparticles, silica microparticles or zirconia microparticles which can highly transmit ultraviolet rays or visible light. The photocatalyst microparticle 21 is constituted of tungsten trioxide microparticles 21a and calcium carbonate microparticles 21b added and stuck to the surface of the tungsten trioxide microparticles 21a. The binder 22 is added in an amount range of 10 to 50% by mass based on the tungsten trioxide microparticles 21a. Also, if acryl-modified silicon or a silicone-based resin is used as the binder 22, a photocatalyst film which is to be cured at 20 to 200° C. can be formed. Also, the calcium carbonate microparticles 21b function as a material adsorbing $NO_x$ (nitrogen oxides) and $SO_x$ (sulfur oxides). Therefore, if it is unnecessary to limit the deterioration of the tungsten trioxide microparticles 21a caused by $NO_x$ and $SO_x$, it is not essential to add and stick the calcium carbonate microparticles 21b.

[Structure of a Deodorizing Unit]

Figure 2A:
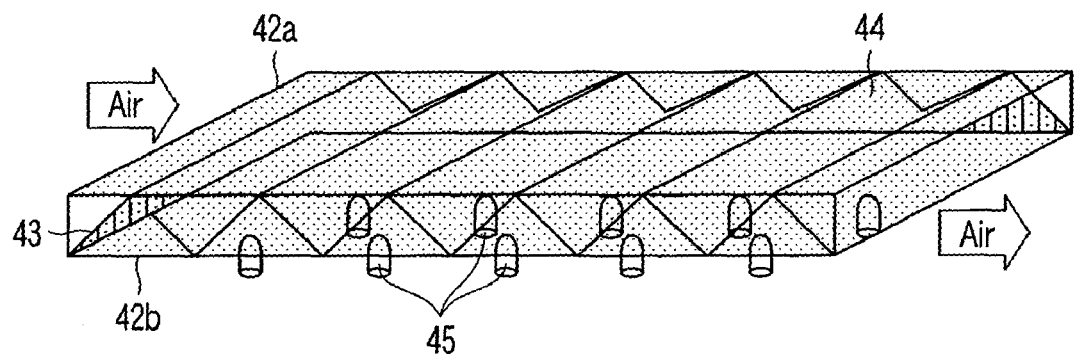
FIG. 2A is a schematic perspective view of a deodorizing unit according to the present invention.
Figure 2B:
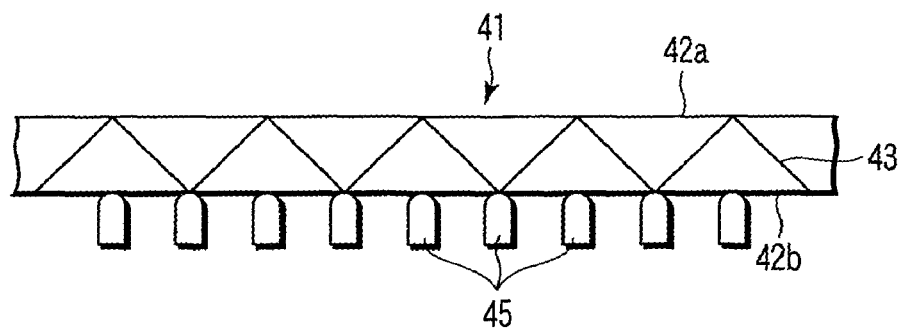
FIG. 2B is a schematic side view of FIG. 2A.

FIGS. 2A and 2B are explanatory views typically showing the structure of a deodorizing unit according to the present invention. Specifically, FIG. 2A is a schematic perspective view of the deodorizing unit and FIG. 2B is schematic side view of FIG. 2A. Here, the tungsten trioxide microparticles are not illustrated for the sake of convenience.

Reference numeral 41 in the figure represents a deodorizing unit as a photocatalyst product. The deodorizing unit 41 is provided with first and second filters 42a and 42b which are upper and lower flat-mesh like filters respectively and a third filter 43 having a sectionally corrugated plate form and disposed between these filters 42a and 42b. The tungsten trioxide microparticles (average particle diameter: 0.1 μm) 44 according to the present invention are supported by the filters 42a, 42b and 43. Plural GaN blue light-emitting diodes 45 are disposed on the underside of the second filter 42b. A white light-emitting diode using a fluorescent body excited by blue light may be disposed in place of this diode 45. In the deodorizing unit having a such a structure, air is brought into contact with the tungsten trioxide microparticles supported by each filter when the air is allowed to flow, for example, from the left side to the right side through the third filter 43 disposed between the first and second filters 42a and 42b, thereby performing deodorization.

Figure 3:
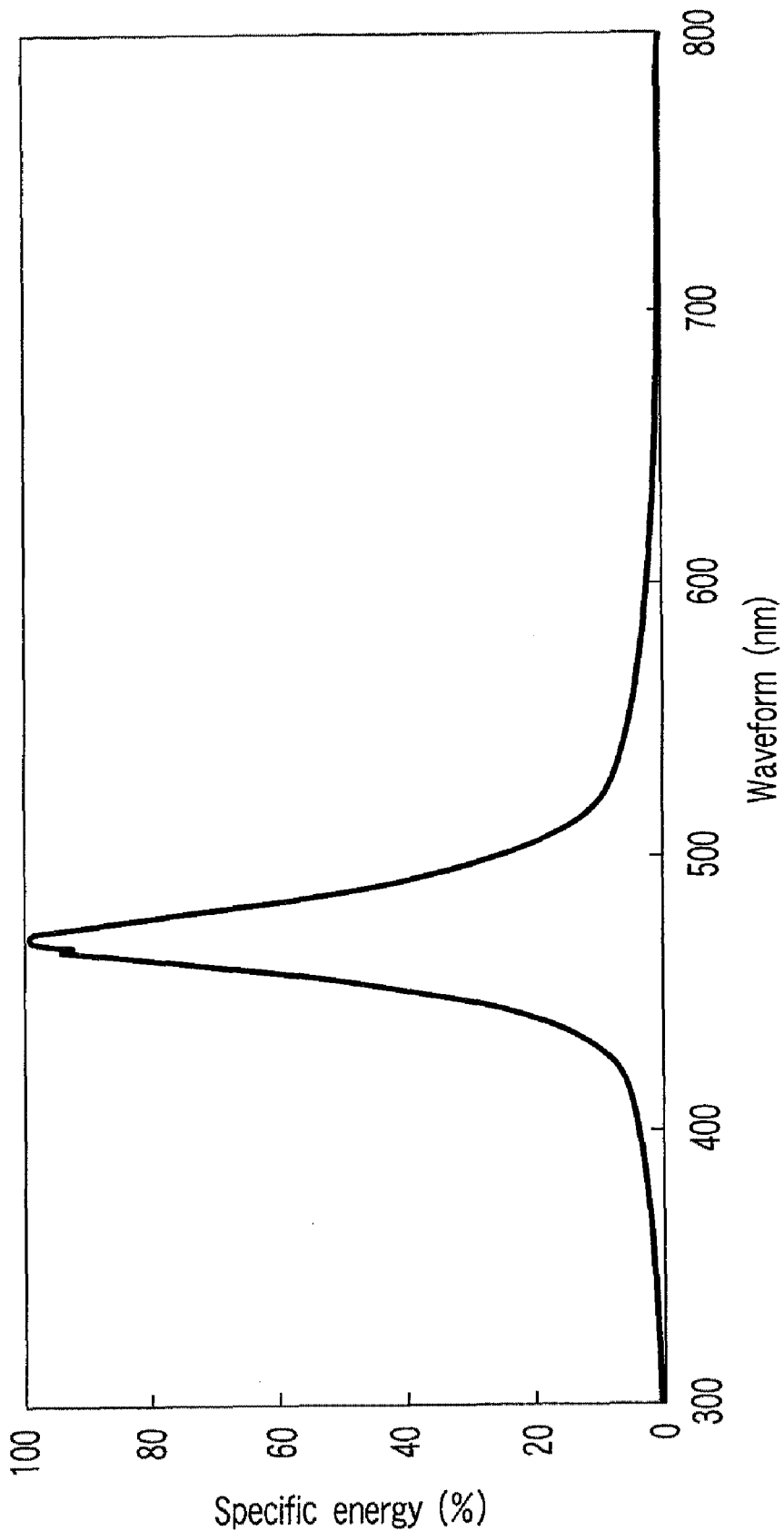
FIG. 3 shows one example of a spectroscopic spectrum of a blue light-emitting diode 45 according to the present invention.

In the present invention, the average particle diameter of the tungsten trioxide ($WO_3$) microparticles is 0.5 μm or less and preferably 0.1 μm or less. Here, when the average particle diameter exceeds 0.5 μm, this reduces the probability of the reaction run on the surface of the microparticles and therefore, only insufficient catalyst effect is obtained. Also, though the crystal structure of the tungsten trioxide microparticles is a monoclinic system, this system is easily transformed into a triclinic system only by grinding these particles in an earthenware mortar and it is therefore important to keep the monoclinic system. FIG. 3 shows the spectroscopic spectrum of the blue light-emitting diode 45 used in the deodorizing unit shown in FIG. 2. It is found from FIG. 3 that the specific energy of the emitted light of the blue light-emitting diode 45 has a peak at a wavelength close to about 470 nm.

FIG. 4 is a graph showing each X-ray diffraction pattern of the triclinic system and monoclinic system of tungsten trioxide ($WO_3$). The X-ray diffraction pattern is measured in the following manner. Specifically, X-ray intensity (CPS) at every diffraction angle (2θ) is measured by a goniometer in which, using CuKα rays (λ=0.15418 nm) as the X-rays, a sample is rotated at an angle of θ with respect to the incident X-rays and at the same time, a detector part constituted of a proportional counter tube is rotated at an angle of 2θ with respect to the incident X-rays. In FIG. 4, the upper side curve shows the case of the triclinic system $WO_3$ and the lower side curve shows the case of the monoclinic system $WO_3$.

As is clear from FIG. 4, when the diffraction pattern of the triclinic system tungsten trioxide with that of the monoclinic system tungsten trioxide, almost all parts of the both are similar. However, it is confirmed that the patterns of the both are largely different in a diffraction angle (2θ) range of 30 to 35°. In particular, there are a high peak specific to the monoclinic system and plural small peaks specific to the triclinic system at a diffraction angle 2=34.155° and therefore, the both curves are clearly different from each other. It is also confirmed that in the case of the monoclinic system tungsten trioxide, two peaks are present in a diffraction angle (2θ) range of 30 to 35°, whereas in the case of the triclinic system tungsten trioxide, three or more peaks are present in the same range. Moreover, as to the ratio of the peak values which appear in a diffraction angle (2θ) range of 30 to 35°, this ratio is as low as 50 to 60% in the case of the triclinic system tungsten trioxide whereas this ratio is 70 to 95% in the case of the monoclinic system tungsten trioxide and a difference in these peak values is small.

Figure 5:
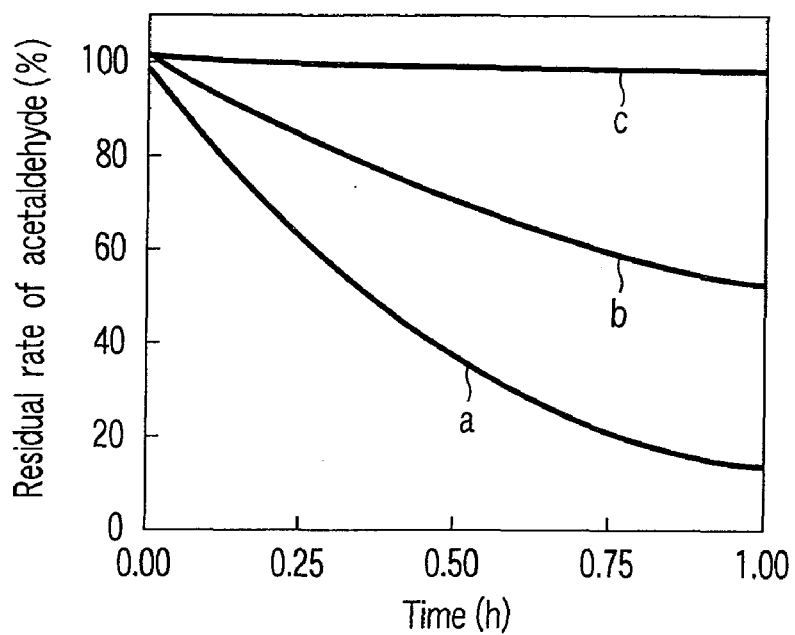
FIG. 5 shows a characteristic diagram for comparing the acetaldehyde gas decomposition effects of tungsten trioxides different in crystal structure.
Figure 6:
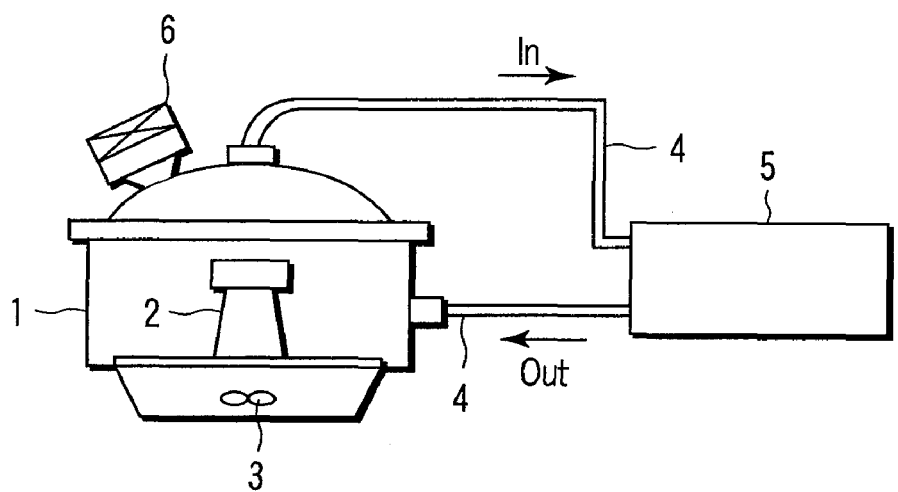
FIG. 6 shown a schematic view of a measuring device used to obtain the characteristic diagram of FIG. 5.

FIG. 5 is a characteristic diagram in which the acetaldehyde gas decomposition effects are compared when the crystal structures of tungsten trioxide are different from each other. In FIG. 5, the line a shows the monoclinic system $WO_3$ microparticles (the lower side of the graph of FIG. 4) of the present invention, the line b shows the triclinic system $WO_3$ microparticles (the upper side of the graph of FIG. 4) which are comparative example and the line c shows the case where no photocatalyst is used and no light is irradiated. FIG. 6 shows a schematic view of a measuring device used to obtain the characteristic diagram of FIG. 5. Reference numeral 1 in the figure represents a desiccator. A Petri dish 2 including a photocatalyst is received in the desiccator 1. A fan 3 is disposed under the Petri dish 2 in the desiccator 1. A multi-gas monitor 5 is connected through a tube 4 on the upper part and side part of the desiccator 1. Also, a blue LED light source 6 that emits light to the photocatalyst is set to the upper oblique position of the desiccator 1.

The above measuring device has the following specification.

Measuring BOX capacity: 3000 cc
Working light source: Blue LED
Measuring unit: Multi-gas monitor
Introduced gas: Acetaldehyde equivalent to 10 ppm
Blue LED: 0.88 $mW/cm^2$ (UV-42)
   0.001 $mW/cm^2$ (UV-35)
Amount of tungsten trioxide microparticles: 0.1 g It is understood from FIG. 5 that the line a has a higher gas decomposition effect than the line b. It is therefore clear that the monoclinic system tungsten trioxide microparticles have a higher photocatalyst effect when visible light is irradiated.

Examples of the photocatalyst paint of the present invention include those having a structure in which the above tungsten trioxide microparticles are used and the tungsten trioxide microparticles keep a monoclinic system crystal structure after the coating is finished. The photocatalyst paint has an excellent function including the removal of VOC of the photocatalyst and is suitable to, for example, a deodorizing filter to be used in air cleaners.

Examples of the photocatalyst body of the present invention include those having a structure in which the above photocatalyst paint is applied to the surface of a base material to form a photocatalyst film. Here, specific examples of the photocatalyst body of the present invention include tubular or globular products such as a fluorescent lamp, building materials such as window glasses, mirrors and tiles, sanitary materials, filter parts of air conditioning equipment and deodorizing apparatuses, and optical devices.

Applicable uses and categories are not limited to these materials.

Examples of the photocatalyst products of the present invention include those having a structure in which the above photocatalyst paint is combined with a GaN blue light-emitting diode or a white light-emitting diode using a fluorescent body excited by blue light and those having a structure in which the above photocatalyst filter is combined with a GaN blue light-emitting diode or a white light-emitting diode using a fluorescent body excited by blue light. Here, the photocatalyst product specifically means, for example, fluorescent lamps, lighting equipment and deodorizing units.

[Apparatus for Producing Photocatalyst Microparticles]

Figure 7:
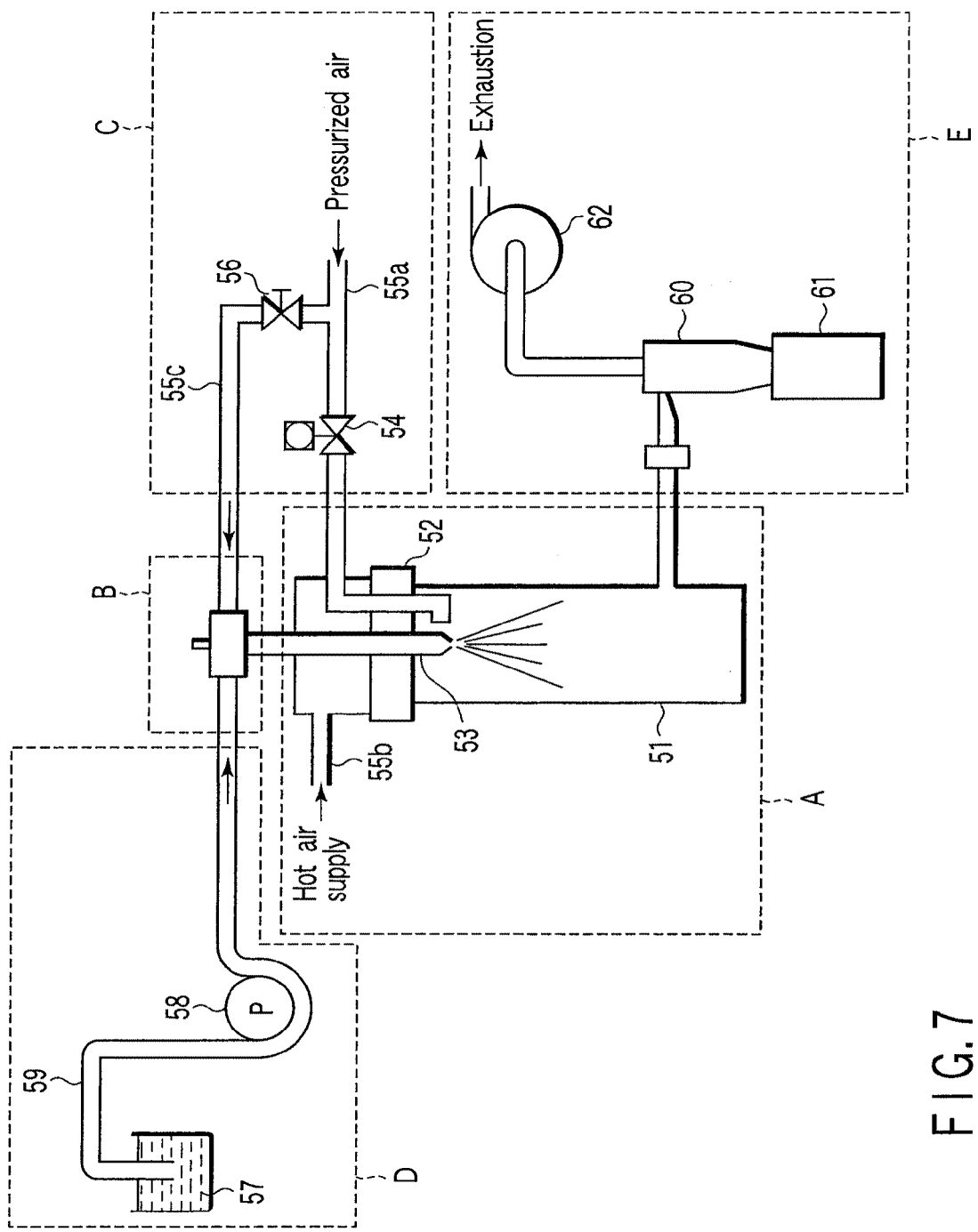
FIG. 7 shows a schematic view of a production apparatus for forming a photocatalyst material according to the present invention.

In the present invention, the photocatalyst microparticles are produced by using, for example, a production apparatus shown in FIG. 7. This production apparatus is constituted of a spray drier body A, a gas-liquid mixing section B, a pressurized air introduction section C, a solution introduction section D and a powder recovery section E. Reference numeral 51 in the figure represents a drying chamber with a distributor 52 disposed in the upper part thereof. Here, the distributor 52 works as an introduction port of air used to heat the drying chamber 51 to 200° C. In the drying chamber 51, a spray nozzle 53 and a pipe 55a equipped with an electromagnetic valve 54 are installed in such a manner as to penetrate through the distributor 52. The pipe 55a works as an introduction port of air that applies pressure to an aqueous solution to sufficiently atomize the aqueous solution. It is also so designed that air is supplied to the upper part of the drying chamber 51 by a pipe 55b. The pipe 55b works as a hot air supply port that supplies hot air for heating the aqueous solution and air. A pipe 55c equipped with a needle valve 56 in the middle thereof diverges from the pipe 55a.

The pipe 55c is connected to the upper part of the spray nozzle 53. A tube 59 that supplies a sample 57 to the inside of the spray nozzle 53 by a pump 58 is connected to the upper part of the spray nozzle 53. It is so devised that the amount of the sample 57 to be supplied to the inside of the spray nozzle 53 can be properly adjusted by the pump 58. A cyclone 60 that extracts the products sprayed in the form of mists from the spray nozzle 53 is connected to the side part of the drying chamber 51. Moreover, a product container 61 that collects the photocatalyst microparticles and an aspirator 62 for exhaustion are connected to the cyclone 60.

A temperature sensor, though not shown, is disposed on each of the inlet side and outlet side of the drying chamber 51. The temperature of the air supplied to the drying chamber 51 and the atmospheric temperature of the photocatalyst microparticles to be supplied to the cyclone 60 are measured by the temperature sensor. Also, the air to be supplied to the inside of the pipe 55c is mixed with the sample 57 to be supplied to the inside of the tube 59 at the upper side of the spray nozzle 53 and the mixed air and solution are sprayed in the form of mists from the bottom of the spray nozzle 53.

When the photocatalyst microparticles are produced using the production apparatus having such a structure, the process is carried out in the following manner. First, 1 to 20% by weight of an aqueous ammonium paratungstate solution (sample) is fed together with the pressurized air to the inside of the spray nozzle 53 and sprayed from the head of the spray nozzle 53 in the form of mists 1 to 10 μm in size in a 200° C. hot air atmosphere to form a granular raw material. At this time, pressurized air is fed from the pipe 55a to the vicinity of the head of the spray nozzle 53 to supply oxygen to the granular raw material sprayed from the spray nozzle 53. Next, the raw material is heat-treated at 700 to 800° C. for 1 to 10 minutes in the drying chamber 51 to form photocatalyst microparticles which contain tungsten trioxide microparticles as their major components, have an average particle diameter of 0.1 μm and have a monoclinic system crystal structure. Then, the photocatalyst microparticles in the drying chamber 51 are collected from the cyclone 60 into the product container 61 while evacuating the drying chamber 51 by the aspirator 62.

The studies made by the inventors of the present invention have revealed that there is a difference in catalyst characteristics among tungsten oxide ($WO_3$) powders. Specifically, the inventors have found that there is a difference in catalyst effect (decomposition ability) among tungsten oxide powders when these powders are irradiated with light having a wavelength of 430 to 500 nm. In the present invention, when the tungsten oxide powder is irradiated with the above light, the tungsten oxide powder is excited.

Specifically, an appropriate tungsten oxide powder is selected based on the catalyst effect (decomposition ability) obtained when light having a wavelength of 430 to 500 nm is irradiated to make it possible to obtain a photocatalyst material having superior characteristics in the present invention. Also, since a tungsten oxide powder having excellent decomposition ability is used, the present invention can provide a photocatalyst product enabling space saving and reduction in weight.

[Photocatalyst Material (First Photocatalyst Material)]

The first photocatalyst material of the present invention is as described in the above (1).

The inventors of the present invention have found that if light having a peak wavelength of 460 nm±10 nm among the wavelengths ranging from 430 to 500 nm is irradiated, the difference in decomposition ability is observed more significantly.

Sunlight is irradiated in which lights ranging from ultraviolet rays to the visible light region (300 to 800 nm) are mixed. For this reason, only light having a wavelength range of 430 to 500 nm cannot be irradiated. Also, a normal fluorescent lamp uses mercury as the exciting source and also uses a calcium halophosphate $(Ba, Ca, Mg)_{10}(PO_4)_6 \cdot C_{12}$:Eu. Such a fluorescent lamp has peak wavelengths in two ranges, 420 to 470 nm and 550 to 580 nm (excluding the peak of mercury itself). White light is obtained by these two lights. In the fluorescent lamp, two lights are intermingled. Therefore, only light having a wavelength range of 430 to 500 nm cannot be irradiated.

For this reason, no study has been made concerning the catalyst effect to be obtained when only the light having a wavelength range of 430 to 500 nm is irradiated. In the case where two or more wavelengths (in this case, wavelengths in blue, green, yellow and red regions) are intermingled, the catalyst effect obtained only by excitations of wavelengths ranging from 430 to 500 nm cannot be confirmed.

The inventors of the present invention have, for the first time, found that there is a difference between tungsten oxide powders in the catalyst effect obtained only by excitation of light having a wavelength range of 430 to 500 nm.

As the light source, a light-emitting diode is suitable. Because the light-emitting diode is a semiconductor element, it uses no mercury unlike a fluorescent lamp. Therefore, it has a mild influence on the environment and therefore, it is being developed as a product substituted for a fluorescent lamp. It has been confirmed that among these diodes, a blue light-emitting diode (B-LED) can supply blue light (wavelength: 430 to 500 nm) stably.

No B-LED has been tried as a light source for a photocatalyst and thus the catalyst effect of a tungsten oxide powder by single light having a wavelength range of 430 to 500 nm has not been verified. In the present invention, a B-LED was used as the light source to investigate the catalyst effect of the tungsten oxide powder. As a result, the inventors of the present invention have found that even if no apparent difference between tungsten oxide powders can be seen, these tungsten oxide powders differ in catalyst effect.

[Photocatalyst Material (Second Photocatalyst Material)]

A second photocatalyst material of the present invention is as described in the above (7).

In the second photocatalyst material, a GaN system light-emitting diode having an emission peak at a wavelength close to 470 nm is preferable as the light source emitting blue light. The average particle diameter of the second photocatalyst material is preferably 10 μm or less. Also, the photocatalyst material preferably contains a monoclinic system as its major phase.

In the present invention, a test for decomposition ability is made in the following manner.

[Test Method for Decomposition Ability to Find the First Photocatalyst Material (First Test for Decomposition Ability)]

1) First, a 3-liter container is prepared as a glass container. Also, as the glass container, a Pyrex (registered trademark, manufactured by Coning Company) glass container which is resistant to the reaction with organic products and the like is desirable though it is not particularly limited as long as it has high airtightness and transmits light having a peak wavelength of 460 nm±10 nm.

2) Next, 1 g of a tungsten oxide powder and 20 ppm (acetaldehyde amount A) of acetaldehyde are poured into the glass container.

3) In succession, acetaldehyde amount B is measured after light having a peak wavelength of 460 nm±10 nm is irradiated to the mixture for 2 hours to measure the decomposition ability (%) based on the following equation.

Decomposition ability (%)=[(acetaldehyde amount $A$−acetaldehyde amount $B$)/acetaldehyde amount $A$]×100.

A multi-gas monitor is used to measure the amount of acetaldehyde.

In the present invention, the initial amount A (20 ppm) of acetaldehyde is a standard and the amount of residual acetaldehyde (acetaldehyde amount B) left after light having a peak wavelength of 460 nm±10 nm is irradiated for 2 hours is measured. Then, a sample in which the residual amount of acetaldehyde is reduced to 50% or less (decomposition ability: 50% or less) is distinguished.

In the test method according to the present invention, it is important that the amount of the tungsten oxide powder is 1 g and the amount of the initial amount of acetaldehyde is 20 ppm. Namely, it is confirmed to what extent a tungsten oxide powder contained in an amount as small as 1 g can decompose 20 ppm of acetaldehyde. At this time, if light having a peak wavelength of 460 nm±10 nm is used, a difference in characteristics is clearly observed.

Also, when the test is made as to the tungsten oxide powder in an amount exceeding 1 g at a time, the amount of acetaldehyde is increased corresponding to that amount. At this time, the glass container may be increased in size according to the need. However, if the amount measured at one time is too large, there is the possibility that the tungsten oxide powder present on the bottom part of the container does not come in contact with acetaldehyde. Therefore, the upper limit of the amount measured at one time is preferably designed to be 500 g. When an amount exceeding 500 g is measured, it is preferable to adopt a method in which the amount is divided into amounts of 500 g or less and preferably 100 g of less to measure.

Also, more simply, an operation to measure a sample in an amount of 1 g which is extracted arbitrarily is carried out ten times (10 places) to deal with this problem. Moreover, as to the condition of arrangement of the powder, it is necessary that the powder be arranged in a thickness of preferably 1 mm or less and more preferably 0.5 mm or less. Here, when the amount of the tungsten oxide powder is less than 1 g, a second test for decomposition ability as will be explained later is preferably applied.

As to the light having a peak wavelength of 460 nm±10 nm, the light preferably has a waveform as shown in FIG. 19 though no particular limitation is imposed on the light as long as it has a peak wavelength in this range. Examples of the light source that provides the waveform as shown in FIG. 19 include a blue light-emitting diode (B-LED). Also, as the waveform, a sharp waveform in which the half value width is 50 nm or less is preferable. When light having a sharp waveform is used, a difference in decomposition ability easily arises when the aforementioned test for decomposition ability is made.

The intensity of the light is preferably 1 mW/cm$^2$ or more. When the intensity of the light is less than 1 mW/cm$^2$, it is difficult to produce the effect to be obtained by irradiating light and it is difficult to exactly determine the decomposition ability. The intensity of the light is preferably 2 to 5 mW/cm$^2$. Even if light having an intensity exceeding 5 mW/cm$^2$ is irradiated, this causes no problem in the test. However, this produces no more effect than that obtained by the light having an intensity of 5 mW/cm$^2$, resulting in a waste of electric power and therefore, the above range is preferable.

An excellent photocatalyst material can be obtained by selecting a photocatalyst material having a decomposition ability of 50% or more and preferably 90% or more and 100% or less by the test of decomposition ability as mentioned above.

[Test Method of Decomposition Ability to Find a Second Photocatalyst Material (Second Test of Decomposition Ability)]

1) First, an airtight container having a capacity of 3 liters is prepared. This airtight container is preferably a glass container and particularly a Pyrex container.

2) Next, 0.1 g of tungsten oxide microparticles (having, for example, an average particle diameter of 0.5 μm or less) is charged in this container.

3) Then, 10 ppm of acetaldehyde is introduced into the container and the tungsten oxide microparticles are irradiated with blue light from a light source to measure the residual amount of acetaldehyde after 30 minutes to find the residual rate. The residual rate (%) is calculated by the following equation:

Residual rate=[(10 ppm−amount ppm of acetaldehyde left after 30 minutes)/10 ppm]×100

Here, the light source emitting blue light is preferably a GaN system light-emitting diode having an emission peak at a wavelength close to 470 nm.

The residual rate is 50% or less and preferably 40% or less. It becomes possible to obtain an excellent photocatalyst material by selecting a material having such characteristics. In the second test of decomposition ability, the measurement time is set to 30 minutes because the amount of the tungsten oxide powder is as small as 0.1 g. When, like the first test of decomposition ability, the amount of the tungsten oxide powder is as relatively large as 1 g, 10 ppm of acetaldehyde is decomposed all at once and it is therefore difficult to find a difference in decomposition ability. Also, the residual amount of acetaldehyde is measured using a multi-gas monitor.

[Third Test of Decomposition Ability]

The first test of decomposition ability and the second test of decomposition ability are methods in which an airtight container is used to measure the decomposition ability in a closed space. As a third test of decomposition ability, on the other hand, there is a method in which measurement is made with flowing gas. Specific examples of such a method include the one according to JIS-R-1701-1 (2004). Though this JIS method is for measuring the ability of removing (decomposition ability) nitrogen oxides, it may be applied to a test of decomposition ability for organic materials such as acetaldehyde.

In the case of carrying out the method according to JIS-R-1701-1, a container defined as "photo-radiation container" in this JIS is preferably used as the above container. The third test of decomposition ability is carried out in the following manner.

1) First, as a measuring sample, 1 g of the photocatalyst material is uniformly applied to a 50×100 mm glass plate, which is then received in the container.

2) Next, air containing 0.1 to 10 ppm of acetaldehyde is allowed to flow as the decomposed gas from a gas supply port of the container at a predetermined flow rate (l/min). Also, the photocatalyst material is irradiated with light having a peak wavelength of 460 nm±10 nm. After the light is irradiated for 60 minutes, the concentration $[I_0]$ of acetaldehyde at the gas supply port of the container and the concentration $[I]$ of acetaldehyde at the gas discharge port of the container are measured. Thereafter, the decomposition ability ($\mu g/m^2$) is found from the following equation:

Decomposition ability=$(K/S)[([I_0]-[I])\times$flow rate (l/min)$\times$irradiation time (60 min)$\times$m]/22.4

In the formula, K is a coefficient that converts $cm^2$ into $m^2$, and specifically K=10000, S is the area of the photocatalyst material on the glass plate and specifically S=50 $cm^2$. The concentration $[I_0]$ of acetaldehyde at the gas supply port of the container and the concentration $[I]$ of acetaldehyde at the gas discharge port of the container are respectively (volume ppm) and m is the molecular weight of acetaldehyde.

The above equation is a method used to measure the absolute value of the amount of acetaldehyde to be decomposed. Also, this equation is given according to JIS-R-1701-1 (2004) 7. Calculation of test results, the formula (I) described in a) Amount of adsorption of nitrogen oxides using a test piece. The decomposition ability may be converted into % from this absolute value. Also, as the light source used to irradiate the light having a peak wavelength of 460 nm±10 nm, a blue LED is preferable.

The third test of decomposition ability is established according to the JIS method and therefore, has high reliability as the measuring method. However, adjusting items including the adjustment of a sample, adjustment of flow rate and initial concentration of acetaldehyde (air containing acetaldehyde) are complicated. For this reason, the first and second tests of decomposition ability are adopted in this invention. The difference in the result of measurement between the first test of decomposition ability and the third test of decomposition ability (converted into % from the measured value) is about ±5%.

The average particle diameter of the photocatalyst material is preferably 10 $\mu$m or less, more preferably 1 $\mu$m or less and even more preferably 0.5 $\mu$m or less. When the average particle diameter is reduced, the surface area of a powder is increased and therefore, the catalyst effect is increased.

In the present invention, the tungsten oxide powder is preferably the one having a monoclinic system as its major phase. The photocatalyst material preferably contains tungsten oxide powder having a monoclinic system as its major phase in an amount of 50% by mass or more and more preferably 70% by mass or more. The tungsten oxide powder includes those having a triclinic system besides those having a monoclinic system. In the tungsten oxide powder (photocatalyst material) used in the present invention, a triclinic system may be intermingled. However, it is desirable that the monoclinic system be contained as the major phase. A tungsten oxide powder containing a monoclinic system as its major phase makes it easy to make selection in the first and second (further, third) tests of decomposition ability.

[Method of Producing a Tungsten Oxide Powder]

Next, a method of producing a tungsten oxide powder will be explained. As the production method, the method in which an appropriate tungsten oxide powder is selected by carrying out the above test of decomposition ability is a most preferable method.

Examples of a method for obtaining the tungsten oxide powder prior to the selection include (a) a method in which metal tungsten is directly oxidized and (b) a method in which a tungsten compound such as ammonium paratungstate (APT) is heat-decomposed in the air to obtain an oxide. A tungsten oxide ($WO_3$) powder can be obtained by any of these methods.

As a production method using APT, the following one may be given as an example. Specifically, first, APT is milled by a beads mill, planetary mill or the like and the milled APT is classified by centrifugation. Next, the obtained microparticles are heat-treated at 400 to 600° C. in the air. A photocatalyst powder including tungsten oxide microparticles having an average particle diameter of 0.01 to 0.5 $\mu$m and a monoclinic type crystal structure can be thereby produced.

Also, other methods include the following methods (1) and (2).

(1) A method including a step of spraying an aqueous 1 to 20 mass % APT solution in a high-temperature atmosphere to produce a granular raw material and a step of heat-treating this granular raw material at 700 to 800° C. for 1 to 10 minutes. By this method, a tungsten oxide powder having a monoclinic system crystal structure is obtained.

(2) A method including a step of carrying out recrystallization after APT is dissolved in an aqueous solvent and a step of baking the obtained crystal at 600° C. or more for 15 seconds or more. A tungsten oxide powder is thereby obtained.

In any of these methods, a monoclinic type tungsten oxide can be obtained by controlling the condition of heat treatment and the like. Here, in the above production method, a tungsten oxide powder having an average particle diameter of 0.1 $\mu$m is obtained. However, when the particle diameter of the obtained tungsten oxide powder is large, the powder is classified to obtain a powder having an average particle diameter of 10 $\mu$m or less and preferably 1 $\mu$m or less.

The photocatalyst material as mentioned above has an excellent photocatalyst effect and can therefore decompose organic materials, $NO_x$, $SO_x$ and the like.

[Photocatalyst Composition]

The photocatalyst composition of the present invention contains the photocatalyst material in an amount of 50% by mass or more as mentioned in the above (11). When the amount of the photocatalyst material is less than 50% by mass, only insufficient photocatalyst effect is obtained. Also, this photocatalyst composition may contain a titanium oxide powder in an amount less than 50% by mass.

[Photocatalyst Product]

The photocatalyst product of the present invention is as described in the above (14). The above photocatalyst composition is suitable for photocatalyst products and has a catalyst effect on at least one of organic compounds, $NO_x$ and $SO_x$.

When the photocatalyst material of the present invention is applied to photocatalyst products, no particular limitation is imposed on the circumstance as long as a light source emitting light having wavelengths including wavelengths ranging from 430 to 500 nm is present. As the exciting source (light source), any light source may be used insofar as it is provided with light having wavelengths including wavelengths ranging from 430 to 500 nm. Examples of the light source include blue light-emitting semiconductor elements (for example, a blue light-emitting diode and blue semiconductor laser), sunlight and various fluorescent lamps. The dose of the light having a wavelength range of 430 to 500 nm is preferably 1 mW/cm$^2$ or more.

Also, when a photocatalyst product is produced, a photocatalyst composition containing the photocatalyst material of the present invention in an amount of 50% by mass or more is allowed if the dose of light having a wavelength range of 430 to 500 nm in the circumstance is as large as 1 mW/cm$^2$ or more and particularly 5 mW/cm$^2$ or more. In this case, it is needless to say that the ratio of the photocatalyst material of the present invention in the tungsten oxide powder is preferably increased to 90% or more and more preferably 100% and namely, the larger the amount of the photocatalyst material, the better.

Also, when used under a light source, such as sunlight, including the ultraviolet region, a photocatalyst composition containing a titanium oxide (TiO$_2$) powder in an amount less than 50% by mass may be used. The photocatalyst product of the present invention is preferably provided with a photocatalyst film formed by binding a tungsten oxide powder with the surface of a substrate by using a predetermined binder. The substrate of the photocatalyst body is to support the photocatalyst film and is originally formed for other functions than those of the photocatalyst material. In other words, the substrate is allowed to be a functional material.

Examples of the functional material include various desired or optional members, for example, building materials such as tiles, window glasses and ceiling panels, kitchen or sanitary materials, domestic instruments, illumination materials, and deodorizing or dust-collecting filters.

When a tungsten oxide powder which is a photocatalyst material is used to form a photocatalyst film, the photocatalyst material may be directly baked to bind this material also with the substrate by sintering. However, if the substrate is bound with the photocatalyst material by a proper binder to form a film, this makes production easy. Also, because the binding operation can be done without exposing the photocatalyst material to high-temperature environment unlike the direct baking, a film can be formed on a substrate less resistant to heat.

When the photocatalyst film is formed from the photocatalyst material by using a binder, for example, silica (SiO$_2$), solder glass, graze, low-melting point metal or thermoplastic synthetic resin may be used as the binder. It is needless to say that in order to bind the photocatalyst material powder (microparticles) with the substrate by baking, it is necessary to use, as the substrate, a material with resistance against the baking temperature.

The primary particles of the tungsten oxide powder which is the photocatalyst material are made to have a particle diameter of 0.001 to 0.1 μm, so that a film having a dense surface can be formed. This also improves visible light transmittance. It is preferable to adopt, as the photocatalyst material, a tungsten oxide powder which has a grain distribution as uniform as possible and is formed of microparticles having a true sphere form. As a result, pores formed as very small clearances in the surface of the photocatalyst film have all the same radius. Therefore, smelly gas having a smaller molecular radius such as acetaldehyde passes through pores in the surface of the photocatalyst film and decomposed rapidly. This structure is also effective for the deodorization and decomposition of acetaldehyde. To the contrary, contaminants such as carbon and tobacco resin, having a particle radius of 0.1 μm or more cannot penetrate into the above pores. However, these contaminants are brought into contact with the surface of the photocatalyst film and decomposed by a redox action.

The functional material means materials originally provided with functions for the purposes different from those of the photocatalyst film. As the functional materials, for example, building materials, sanitary machinery and tools, kitchen machinery and tools, filters for equipment, machinery and tools for domestic use, illumination materials fall in this category. Examples of the building materials include tiles, floor materials, window materials and wall materials. Examples of the sanitary machinery and tools include wash stands, baths and toilets for feces or urine. Examples of the kitchen machinery and tools include sinks, cooking tables and cupboards.

Examples of the filters for equipment include air cleaner filters, bath circulation filters, air conditioner filters, heating filters and deodorizing apparatus filters. A structure is considered in which a filter provided with holes through which a fluid passes is used as a substrate and a photocatalyst film containing, as its major component, a tungsten oxide powder is formed on the surface of the substrate. In the case of this structure, air passing through this filter flows while contacting with the photocatalyst body having as wide an area as possible. For this reason, the deodorizing effect can be improved. Also, a bactericidal effect can also be produced. Also, the filter and the photocatalyst body may be formed separately to constitute a deodorizing apparatus. Specifically, the photocatalyst body and the filter are separately disposed in the passage to allow fluid air to be in contact with the photocatalyst body.

Also, the present invention allows a structure in which a deodorizing apparatus is provided in equipment besides the structure in which the deodorizing apparatus is singly used. For example, the deodorizing function provided in refrigerators, air conditioners, coolers, heaters, air cleaners, humidifiers or dehumidifiers may be handled as deodorizing apparatuses.

Examples of the domestic instruments include refrigerators, washing machines, microwave ovens, dishwashers, coffee makers and vacuum cleaners.

Examples of the lighting equipment include lamps such as fluorescent lamps, shades/globes for lighting equipment, translucent covers, chandelier covers, reflecting plates and sockets.

Though the lighting equipment is suitable for interior uses because it has such a significant action as to be able to decompose VOC which becomes problematic indoors, it is also suitable for outdoor lighting equipment because it has the ability to decompose contaminants together.

If the photocatalyst of the present invention is applied to machinery and tools for domestic use, illumination materials or lighting equipment, machinery and tools for domestic use, illumination materials or lighting equipment which has photocatalyst effects such as deodorizing functions may be produced.

The lighting equipment body means a remainder part obtained by removing a lamp from the lighting equipment. It is well known that lighting equipment takes various structures and shapes which are adopted according to a difference in uses, for example, indoor use or outdoor use, or domestic use or business use, and also according to decorations and designs. Along with this, appropriate light control means is selected from a reflecting plate, translucent cover, louver, shade/globe and the like. Therefore, it is out of consideration whether or not the lighting equipment body is provided with structures of light control members such as a reflecting plate and translucent cover. However, the lighting equipment body is almost commonly provided with a part supporting a lamp, a part connecting a light source and a part setting a lighting equipment.

A photocatalyst film using a functional material as the substrate and containing a tungsten oxide powder as its major component is formed in this manner. Therefore, while the photocatalyst film is used, it is activated when irradiated with light including at least visible rays. As a result, the photocatalyst film exerts actions such as a deodorizing action, anti-contaminating action and antibacterial action together and therefore, produces such effects as to improve sanitation in living spaces and to achieve easy cleaning.

Next, specific embodiments according to the present invention will be explained.

FIRST EMBODIMENT

A photocatalyst powder according to a first embodiment was produced in the following manner.

First, ammonium paratungstate (APT) was milled by a beads mill or planetary mill and classified by centrifugation. Next, the obtained microparticles were heat-treated at 400 to 600° C. in the atmosphere, thereby making it possible to produce and refine a photocatalyst powder constituted of tungsten trioxide microparticles having an average particle diameter of 0.01 to 0.5 μm and a monoclinic system crystal structure. In this embodiment, monoclinic system tungsten trioxide microparticles having an average particle diameter of about 0.1 μm were obtained by carrying out heat treatment at about 500° C. in the atmosphere. The data of grain distribution in this step is as shown in FIGS. 8 and 9. Here, FIG. 8 is a view showing grain distribution (relation among particle diameter, and frequency and cumulative undersized particles) after particles are dispersed. FIG. 9 is a graph showing the grain distribution (relation among particle diameter, frequency and cumulative undersized particles) of a $WO_3$ dispersed paint. It has been clarified from FIGS. 8 and 9 that crystals grow a little with increase in grain size by heat treatment.

According to the photocatalyst powder in the first embodiment, it contains, as its major component, tungsten trioxide microparticles having an average particle diameter of 0.1 μm and has a monoclinic system crystal structure. Therefore, a visible light-responsive type photocatalyst powder which can significantly improve the photocatalyst performance is obtained.

SECOND EMBODIMENT

A photocatalyst paint for indoor use according to a second embodiment was produced in the following manner.

First, tungsten trioxide microparticles and a minute amount of a surface treating agent were mixed in an organic solvent (ethyl alcohol) and the mixed solution was subjected to dispersing treatment using a beads mill for several hours. In succession, an inorganic binder (polysiloxane) in an amount of 30% by mass based on the tungsten trioxide microparticles, an organic solvent (alcohol) and several % of purified water were added to the solution to redisperse, thereby producing a photocatalyst paint. After that, calcium carbonate and magnesium hydroxide were added to the obtained photocatalyst paint in several levels of amounts ranging from 0.1 to 10 mol % based on tungsten trioxide, and then, each obtained solution was stirred to make samples. Next, each sample paint was applied to a glass plate, acryl plate and fluorescent lamp glass tube and dried at 120 to 180° C. to make paint samples.

These paint samples in the initial state were placed in a 1 m³ stainless box. The glass plate and acryl plate were respectively irradiated with ultraviolet rays from a BLB lamp at a dose of 1 mW/cm² and the fluorescent lamp was turned on as it was in the box to measure the effect of decomposing formaldehyde. With regard to the measured samples, the glass plate and the acryl plate were allowed to stand in a room and the fluorescent lamp was subjected to a lighting test in a usual office to measure the gas decomposition ability of each sample every week.

According to the second embodiment, magnesium oxide that absorbed $SO_x$ and $NO_x$ more easily than tungsten trioxide was added properly to a paint containing tungsten oxide microparticles to make a structure in which a photocatalyst film constituted of the obtained indoor photocatalyst paint was formed into a fluorescent lamp. This structure ensures that not only the effects such as sterilization and anti-contamination, which are specific to a photocatalyst are obtained but also the deterioration of the photocatalyst film during use can be limited, thereby obtaining a fluorescent lamp having a long life.

THIRD EMBODIMENT

First, for example, an aqueous 4 mass % ammonium paratungstate solution (sample) is fed in the spray nozzle 53 shown in FIG. 7 together with pressurized air, which is then sprayed from the head of the spray nozzle 53 in an atmosphere of 200° C. hot air in the form of mists having a particle diameter of 1 to 10 μm to produce a granular raw material. At this time, pressurized air is fed from the pipe 55*a* to the vicinity of the head of the spray nozzle 53 to supply oxygen to the photocatalyst microparticles sprayed from the spray nozzle 53. When the concentration of the aqueous solution is 4% by mass, a granular raw material of ammonium paratungstate having a particle diameter of 0.04 to 0.4 μm is obtained. Next, the granular raw material is subjected to rapid short-time heat treatment carried out at 800° C. for 1 to 10 minutes in the drying chamber 51 to forcibly dry the raw material to recrystallize. Tungsten trioxide photocatalyst microparticles are formed which contain tungsten trioxide microparticles as their major components and have an average particle diameter of 0.5 μm or less and preferably 0.1 μm or less and a monoclinic system crystal structure. In succession, the photocatalyst microparticles in the drying chamber 51 are collected into the product container 61 through the cyclone 60 while evacuating the drying chamber 51 by the aspirator 62.

According to the third embodiment, pressurized air is fed to the vicinity of the head of the spray nozzle 53 from the pipe 55*a* to supply oxygen to the photocatalyst microparticles, whereby $WO_3$ crystal photocatalyst microparticles reduced in oxygen defect can be obtained. Also, the granular raw material is subjected to rapid short-time heat treatment carried out at 800° C. for 1 to 10 minutes in the drying chamber 51, whereby $WO_3$ crystal photocatalyst microparticles reduced in crystal growth can be obtained.

Figure 10:
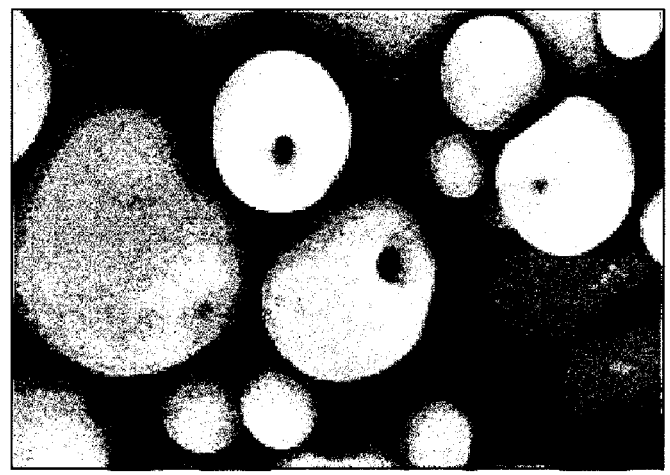
FIG. 10 shows a microphotograph of ammonium metatungstate as a granular raw material obtained in a third embodiment.
Figure 11:
FIG. 11 shows a microphotograph of a monoclinic system type WO$_3$ crystal photocatalyst microparticles obtained by heat-treating a granular raw material obtained in the third embodiment by means of rapid heating carried out at 800° C. in as short a time as 1 to 10 minutes.

FIG. 10 shows a microphotograph of ammonium metatungstate obtained as the granular raw material in the third embodiment. FIG. 11 shows a microphotograph of the monoclinic system type $WO_3$ crystal photocatalyst microparticles obtained by subjecting the granular raw material obtained in the third embodiment to rapid short-time heat treatment carried out at 800° C. for 1 to 10 minutes. It is understood from FIG. 10 that an ammonium metatungstate granular raw material made of particles having almost the same particle diameter is obtained though a little difference between these diameters is observed.

FOURTH EMBODIMENT

The microparticles of this embodiment are tungsten trioxide microparticles produced by heating/baking a raw material at high temperature for one minute in the atmosphere, the raw material being obtained by dissolving commercially available ammonium paratungstate in an aqueous solvent, followed by recrystallizing.

FIG. 12 is a characteristic diagram showing the acetaldehyde gas decomposition ability of each tungsten trioxide photocatalyst microparticle when the baking temperature is varied to 600° C., 70° C., 800° C. and 900° C. in the fourth embodiment. FIG. 13 is a characteristic diagram showing the acetaldehyde gas decomposition ability of each tungsten trioxide photocatalyst microparticle when the baking temperature is varied to 800° C., 900° C. and 1000° C.

The evaluation of decomposition ability as shown in FIGS. 12 and 13 was made in the following condition. First, 0.1 g of tungsten trioxide microparticles was placed in a Petri dish, which was then put in a closed container having a capacity of 200 cc. Then, a blue LED was installed in the container such that the photocatalyst microparticles can be irradiated with light having an emission spectrum as shown in FIG. 3. Then, acetaldehyde gas was introduced such that the concentration of acetaldehyde in the container was 10 ppm and at the same time, the blue LED was tuned on to measure a variation in gas concentration every passage of time. The concentration was measured based on the output of a gas sensor installed in the container to evaluate the concentration by relatively comparing these outputs. In the graphs of FIGS. 12 and 13, the ordinate is the relative value (%) showing the output of the sensor corresponding to the concentration of acetaldehyde. These figures clearly show the situation where gas is filled in the container in 20 to 30 seconds after it is introduced into the container and then, the concentration of gas is dropped gradually due to the decomposing effect of the photocatalyst. In FIGS. 12 and 13, the maximum value of the sensor output is defined as 100% for the sake of convenience.

According to the results shown in FIGS. 12 and 13, it is found that the decomposition effect is the highest when crystals obtained by dissolving the commercial product, ammonium paratungstate which is the raw material, in water and micronizing ammonium paratungstate by recrystallization are baked at 800° C. and that the baking temperature is preferably 700 to 900° C. As mentioned above, the photocatalyst material of this embodiment is superior in response to visible light to tungsten oxide obtained only by baking a commercially available product and can be improved in photocatalyst activity.

FIFTH EMBODIMENT

The microparticles of this embodiment are tungsten trioxide microparticles produced by heating/baking particles at 800° C. for a specified time in the atmosphere, the particles being obtained by dissolving commercially available ammonium paratungstate in an aqueous solvent, followed by recrystallizing.

Figure 14:
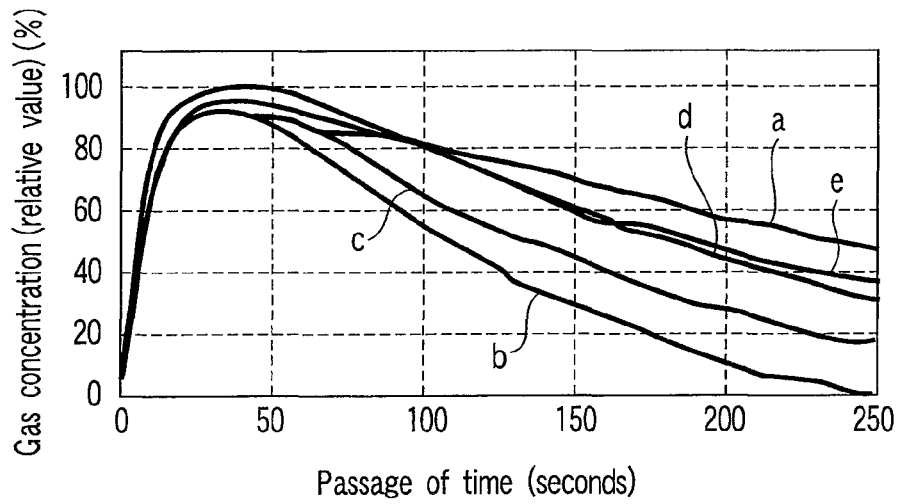
FIG. 14 is a characteristic diagram showing the acetaldehyde decomposition ability of each tungsten trioxide photocatalyst microparticle when the baking time is varied to 30 seconds, 1 minute, 5 minutes, 10 minutes and 15 minutes.

FIG. 14 is a characteristic graph showing the acetaldehyde gas decomposition ability of the tungsten trioxide photocatalyst microparticles when the baking time is varied to 30 seconds (line (a)), 1 minute (line (b)), 5 minutes (line (c)), 10 minutes (line (d)) and 15 minutes (line (e)). The evaluation condition of decomposition ability and the contents of notation of the graph are the same as those in FIGS. 12 and 13.

According to the results of FIG. 14, it is found that high gas decomposition ability is obtained when the baking time is 1 to 5 minutes.

SIXTH EMBODIMENT

Figure 16:
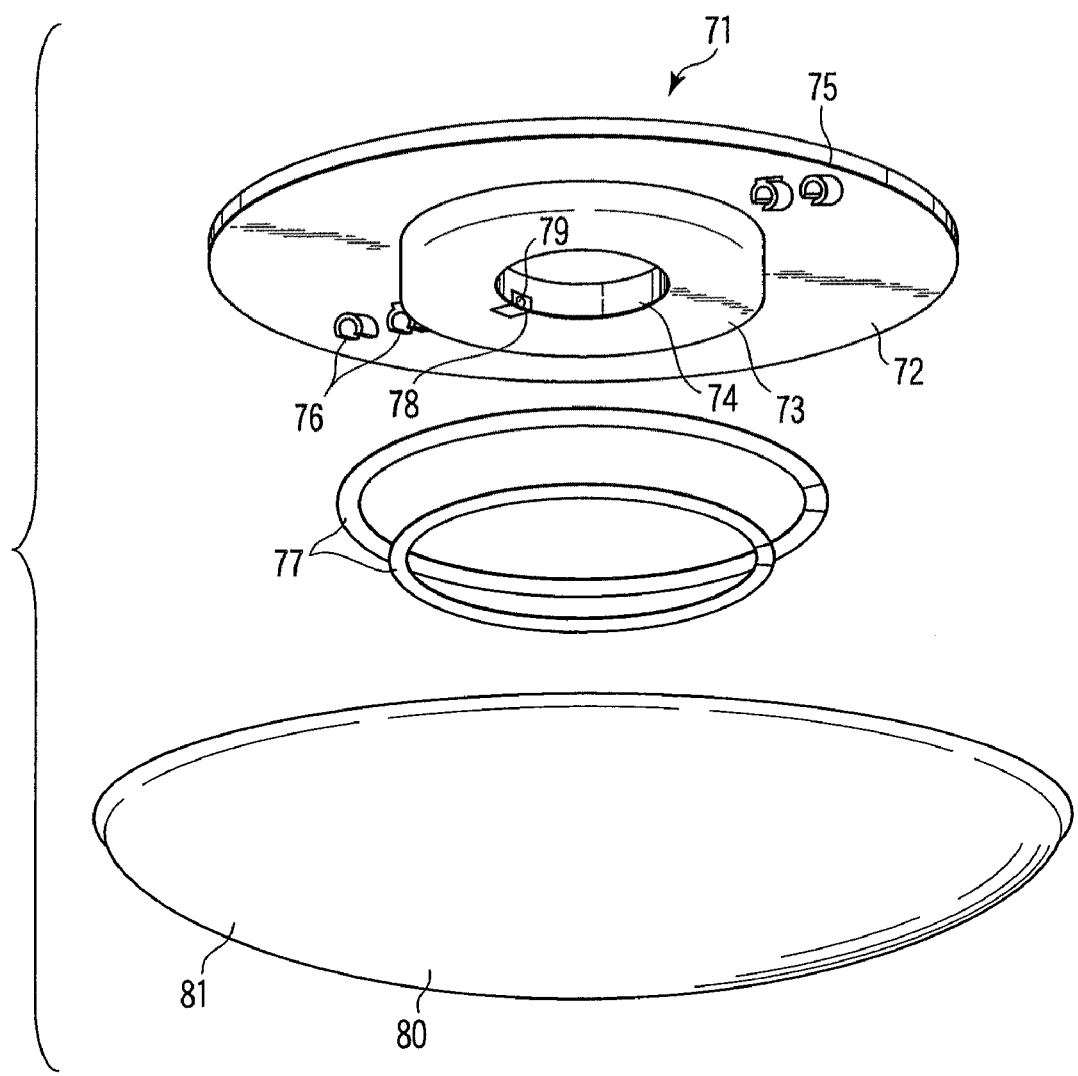
FIG. 16 shows a perspective view of the disassembled state of a lighting equipment according to the sixth embodiment.
Figure 17:
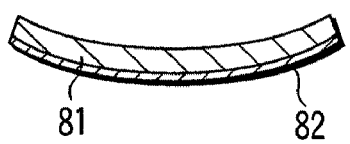
FIG. 17 shows an enlarged sectional view of an essential part of FIG. 16.
Figure 24:
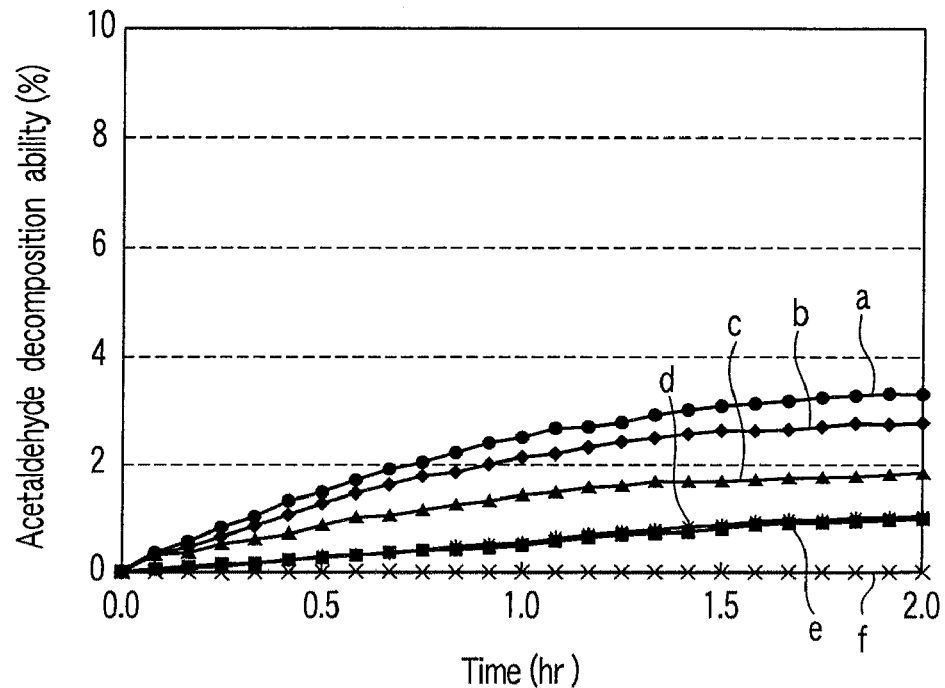
FIG. 24 shows a first decomposition ability test when samples 1 to 6 according to this embodiment are excited by a green light-emitting diode.

A lighting equipment according to a sixth embodiment of the present invention has a structure as shown in FIGS. 16 and 17. Here, FIG. 16 is a perspective view of the disassembled state of the above lighting equipment and FIG. 17 is an enlarged sectional view of the essential part of FIG. 16. This embodiment relates to a lighting equipment using a transmittable shade (cover) formed with an ultraviolet-ray cutting layer primarily including an ultraviolet shielding material on the inside surface thereof.

A lighting equipment 71 is provided with an equipment body 72 directly installed on the ceiling via a hook ceiling attached to the ceiling and an adapter attached to the hook ceiling. This equipment body 72 has a disk form and is provided with a step part 73 having a large thick-dimension in the center thereof and is also provided with a circular opening 74 in the center of the step part 73 to insert and mechanically connect the adapter.

Also, two lamp sockets 75 and two lamp holders 76 are provided in the peripheral parts of the equipment body 72. Two circular light-emitting tubes 77 of a fluorescent lamp which are to be a light source, for example, 32 W and 40 W light-emitting tubes different in outside diameter from each other, which are electrically and mechanically connected to the lamp sockets 75 and mechanically supported by the lamp holders 76, are arranged concentrically so as to surround the step part 73. Also, a socket 78 is formed on the part of the opening 74 and a lamp 79 such as a baby bulb is attached to this socket 78. A shade 80 as an illumination optical part is detachably attached to the equipment body 72 so as to cover the under part and side part of the equipment body 72 and the members attached to the equipment body 72. The shade 80 is provided with an acryl cover base material 81 for illumination which is formed of a translucent material such as glass or a resin in a curved surface form expanded smoothly downward. A photocatalyst layer 82 made of tungsten trioxide microparticles having a monoclinic system crystal structure and an average particle diameter of 0.1 μm is formed on the outside surface of the base material 81. Here, the photocatalyst layer 82 is formed in the following manner. First, ammonium paratungstate (APT) about 100 μm in particle diameter, which is a raw material and a commercially available product is milled into particles having an average particle diameter of 0.05 to 0.1 μm by a beads mill or a planetary mill and then, the obtained microparticles are heated at 500° C. for 8 hours in the atmosphere to produce tungsten trioxide microparticles. Next, these tungsten trioxide microparticles and a binder component are subjected to dispersion mixing treatment using a solvent to make a paint, which is then applied to the base material 81 by a spray gun, followed by drying to thereby form the photocatalyst layer.

According to the sixth embodiment, the photocatalyst layer 82 is formed on the surface of the base material 81 by using the paint in which tungsten trioxide microparticles and a binder component are dispersed, and it is therefore unnecessary to carry out heating treatment at a high temperature after forming a film. Therefore, a photocatalyst function can be provided to a subject to be coated even if the subject is a base material such as an organic base material and sufficient activity can be obtained even in the case of coating the outside surface of an acryl cover.

It is to be noted that in the sixth embodiment, the photocatalyst layer 82 is formed on the outside surface of the base material 81. However, the photocatalyst layer is not limited to the above structure and may be formed as an integrated body by, for example, mixing a photocatalyst material in a resin constituting the base material 81.

Figure 15:
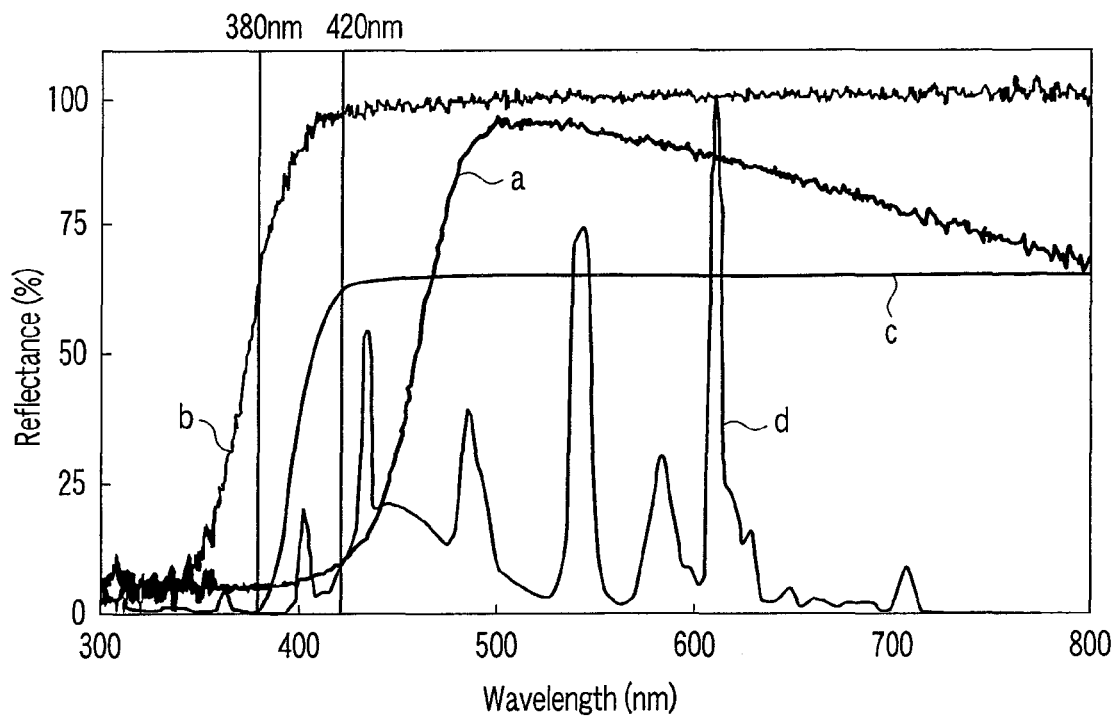
FIG. 15 shows the relation between wavelength and reflectance when a $WO_3$ photocatalyst in a sixth embodiment is used or when a $TiO_2$ photocatalyst is used.

FIG. 15 is a view showing the relation between the wavelength and the reflectance in the case of using a $WO_3$ photocatalyst (line a) and in the case of using a $TiO_2$ photocatalyst (curved line b) in the sixth embodiment. The curved line c in FIG. 15 shows the transmittance of an acryl cover and the curved line d shows the spectral distribution of light emitted from a three-wavelength type fluorescent lamp. As is clear from the graph of FIG. 15, it is understood that tungsten trioxide in this embodiment efficiently absorbs visible light ranging from blue light to bluish green light having a wavelength from 400 to 500 nm and transmitted by the acryl cover as energy activating a photocatalyst.

SEVENTH EMBODIMENT

This embodiment is a structure in which a $WO_3$ photocatalyst layer is formed on a reflecting plate base material made of a color steel plate for illumination. The photocatalyst layer was formed in the following manner. Specifically, first, ammonium paratungstate (APT) about 100 µm in particle diameter, which is a raw material and a commercially available product is milled into particles having an average particle diameter of 0.05 to 0.1 µm by a beads mill or a planetary mill and then, the obtained microparticles are heated at 500° C. for 8 hours in the atmosphere to produce tungsten trioxide microparticles. Next, these tungsten trioxide microparticles and a binder component are subjected to dispersion mixing treatment using a solvent to make a paint, which is then applied to the reflecting plate base material made of a steel plate by a spray gun, followed by drying to thereby form the photocatalyst layer.

The seventh embodiment has the same effect as the sixth embodiment.

FIG. 18 is a characteristic diagram showing the relation between time and acetaldehyde residual rate of a lighting equipment in the seventh embodiment and a fluorescent lamp with a $TiO_2$ photocatalyst (line a), a fluorescent lamp with a $TiO_2$ photocatalyst (line b) and a lighting equipment with $TiO_2$ photocatalyst and a fluorescent lamp with a $TiO_2$ photocatalyst (line c). As is clear from the graph of FIG. 18, the photocatalyst layer formed on the surface of the reflecting plate base material of the lighting equipment is superior in photocatalyst effect when the photocatalyst layer is formed using monoclinic system tungsten trioxide microparticles to when the photocatalyst layer is formed using conventional $TiO_2$ microparticles.

EIGHTH EMBODIMENT

First, an ammonium paratungstate powder was decomposed under heating in the air to produce an oxide, thereby obtaining tungsten oxide ($WO_3$) powder. Next, this powder was classified to obtain a tungsten oxide powder having an average particle diameter of 0.2 µm. In succession, baking and classifying operations were repeated several times to prepare tungsten oxide powders different in lot, which were each mixed and uniformed in such a manner as not to damage the powder, thereby making samples 1 to 5.

Next, five Pyrex containers (3 liters) were prepared and 1 g of a powder was extracted from each sample and poured into the container together with 20 ppm of acetaldehyde. A blue light-emitting diode (blue LED) having a peak wavelength of 460 nm was prepared and light thereof is irradiated to the container for 2 hours to measure the amount of acetaldehyde by a multi-gas monitor, thereby finding decomposition ability (%) (the first test for decomposition ability was adopted).

Also, the light source was changed to sunlight, a fluorescent light (a usual fluorescent lamp using a calcium halophosphate fluorescent body; trade name: FL20SS manufactured by Toshiba Lighting & Technology Corporation) or a green light-emitting diode having a peak wavelength of 530 nm (the peak wavelength is shown in FIG. 20) to measure the decomposition ability together. The results are shown in Table 1 below. The dose of light was standardized to 3 $mW/cm^2$ in the case of a blue light-emitting diode (blue LED, wavelength: 460 nm), fluorescent lamp (wavelength: 400 to 650 nm) and green light-emitting diode (green LED, wavelength: 530 nm). The dose of sunlight (wavelength: 300 to 800 nm) was 10 $mW/cm^2$.

Also, for comparison, a sample using a titanium oxide powder having an average particle diameter of 0.2 µm was also measured. In Table 1, the samples 1 to 4 are examples of the present invention, the sample 5 is a comparative example using tungsten oxide which is not provided with the decomposition ability of the present invention and the sample 6 is a comparative example measured using a titanium oxide powder having an average particle diameter of 0.2 µm.

TABLE 1

| | Decomposition ability when light source is changed (%) | | | |
| --- | --- | --- | --- | --- |
| | Blue LED | Sunlight | Fluorescent lamp | Green LED |
| Sample 1 | 100 | 72 | 70 | 2 |
| Sample 2 | 92 | 70 | 67 | 2 |
| Sample 3 | 80 | 66 | 65 | 1 |
| Sample 4 | 55 | 45 | 43 | 1 |
| Sample 5 | 33 | 27 | 26 | 1 |
| Sample 6 | 0.2 | 10 | 3 | 0 |

Also, the test results of decomposition ability are described when each sample was excited by a blue LED (FIG. 21), sunlight (FIG. 22), a fluorescent lamp (FIG. 23) and green LED (FIG. 24) (the abscissa is the time (min.) and the ordinate is the decomposition ability (%)). In FIGS. 21 to 24, the lines a, b, c, d, e and f show the samples 1, 2, 3, 4, 5 and 6, respectively.

As is clear from Table 1 and FIGS. 21 to 24, it has been found that the photocatalyst materials such as the samples 1 to 4 which each give better characteristics due to the decomposition ability of a blue LED also give better characteristics when irradiated with sunlight or light from a fluorescent lamp.

On the other hand, when the result of decomposition ability obtained by a blue LED was less than 50% as in the case of the sample 5, good results were not obtained also when the sample was irradiated with sunlight or light from a fluorescent lamp. Also, when the light, like a green LED, having no peak wavelength in wavelength range of 430 to 500 nm was used, the decomposition ability of the sample was hardly developed. Moreover, it was also found that there is a difference in the decomposition ability between lots even if the production method was the same. Therefore, it is effective to select by the test of decomposition ability according to the present invention.

NINTH EMBODIMENT

The results measured by the second test of decomposition ability are shown. First, samples 7 and 8 were obtained each as a tungsten powder having an average particle diameter of 0.1 µm by the same method as in the eighth embodiment. Next, three Pyrex containers (3 liters) were prepared and 0.1 g of tungsten oxide powder was extracted from the above sample, weighed and put in each container. In succession, 10 ppm of acetaldehyde was introduced and then, the tungsten oxide powder was irradiated with blue light by using a blue LED having a peak wavelength of 470 nm to measure the residual amount of acetaldehyde by using a multi-gas monitor after 0.5 hours (30 minutes), thereby finding the residual rate.

The results are as shown in FIG. 5 mentioned above. In FIG. 5, the line a shows the sample 7, the line b shows the sample 8 and the line c shows a comparative example in which no photocatalyst is used and no light is irradiated. The residual rate when the irradiation time is 0.5 hours is 38% in the case of the sample 7 (example), 70% in the case of the sample 8 (comparative example) and 99% in the case of comparative example.

Also, when the X-ray diffraction patterns of the samples 7 and 8 were observed, the sample 7 had a monoclinic system as its major phase and the sample 8 had a triclinic system as its major phase. From these results, it may be said that the tungsten oxide powder preferably has a monoclinic system as its major phase.

TENTH EMBODIMENT

The first test of decomposition ability was made in the same manner as in the eighth embodiment by using the same sample as the sample 2 except that the average particle diameter was different. The results are shown in Table 2 shown below.

TABLE 2

|  | Average particle diameter (µm) | Decomposition ability when light source is changed (%) | | | |
|---|---|---|---|---|---|
|  |  | Blue LED | Sunlight | Fluorescent lamp | Green LED |
| Sample 2 | 0.2 | 92 | 70 | 67 | 2 |
| Sample 9 | 0.05 | 95 | 75 | 74 | 3 |
| Sample 10 | 1.0 | 90 | 68 | 66 | 2 |
| Sample 11 | 5.0 | 86 | 63 | 61 | 1 |

It is found from Table 2 that as the particle diameter is decreased, the characteristics are more improved.

ELEVENTH EMBODIMENT

In this embodiment, the first test of decomposition ability in which the dose of light to be irradiated was changed was made by using the sample 2 to examine a variation in decomposition ability. The results are shown in Tables 3 and 4.

TABLE 3

|  | Decomposition ability when dose of light from blue LED is changed (%) | | | | |
|---|---|---|---|---|---|
| Dose of light (mW/cm$^2$) | 0.1 | 1 | 3 | 5 | 10 |
| Sample 2 | 40 | 90 | 92 | 95 | 96 |

TABLE 4

|  | Decomposition ability when dose of fluorescent lamp is light from changed (%) | | | | |
|---|---|---|---|---|---|
| Dose of light (mW/cm$^2$) | 0.1 | 1 | 3 | 5 | 10 |
| Sample 2 | 30 | 66 | 67 | 70 | 72 |

Figure 25:
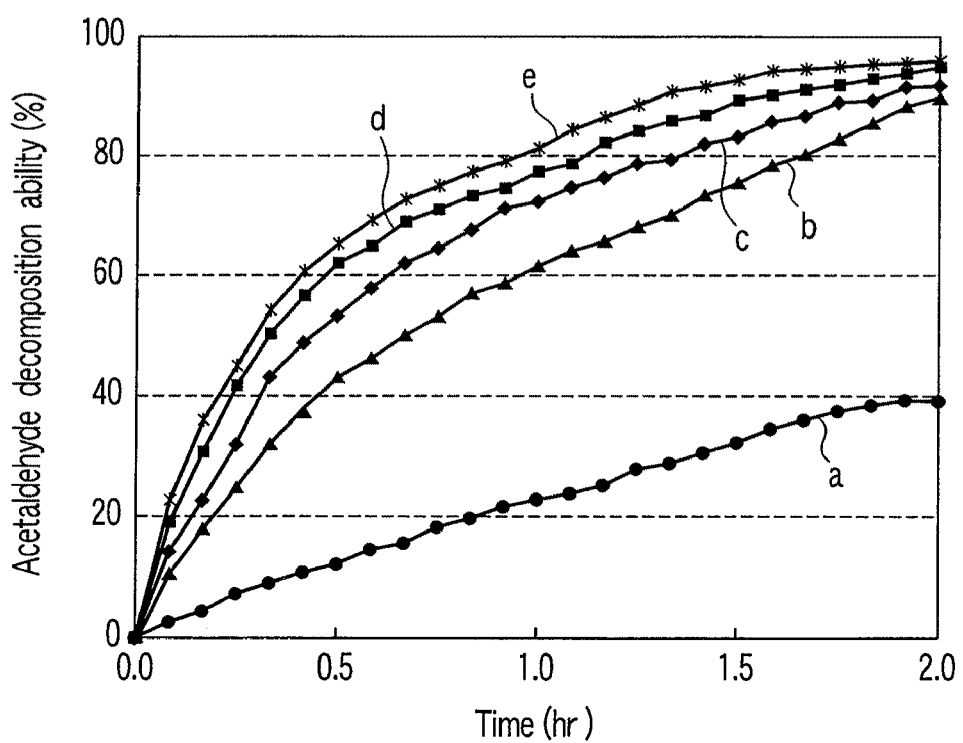
FIG. 25 shows one example of a first decomposition ability test of a sample 2 according to this embodiment when the dose of light emitted from a blue light-emitting diode is changed.

It is understood from Tables 3 and 4 that the dose of light is preferably 1 mW/cm$^2$ or more. Also, the results of the test of decomposition ability when the dose of light from the blue light-emitting diode is varied as shown in Table 3 are illustrated in FIG. 25. The lines a, b, c, d, e and f show the results when the dose (mW/cm$^2$) of light to be irradiated are 0.1, 1, 3, 5 and 10. It is understood from FIG. 25 that as the dose of light is increased, the rate of decomposition is increased. However, it has been found that when the dose of light exceeds 5 mW/cm$^2$, no significant difference in the rate of decomposition is observed.

TWELFTH EMBODIMENT

First, the WO$_3$ powder of the sample 2 and the TiO$_2$ powder of the sample 6 were mixed in predetermined amounts to prepare photocatalyst compositions. Then, each sample having different mixing ratio was subjected to the first test of decomposition ability in which each sample was excited by a blue LED or sunlight to examine a difference in ability. The results are shown in Table 5 below.

TABLE 5

|  | Ratio of WO$_3$ powder | Ratio of TiO$_2$ powder | Decomposition ability when light source is changed (%) | |
|---|---|---|---|---|
|  | (mass %) | (mass %) | Blue LED | Sunlight |
| Sample 12 | 80 | 20 | 90 | 75 |
| Sample 13 | 60 | 40 | 85 | 70 |
| Sample 14 | 20 | 80 | 77 | 35 |

It is found from Table 5 that when the WO$_3$ powder is mixed with the TiO$_2$ powder, the decomposition ability exerted when excited by light including an ultraviolet region, such as sunlight, is improved. However, when the content of the TiO$_2$ powder exceeds 50% by mass, characteristics obtained are similar to those obtained by using only the TiO$_2$ powder, in which case mixing with the WO$_3$ powder exerts almost no effect of the invention.

THIRTEENTH EMBODIMENT

In this embodiment, the WO$_3$ powder of the sample 2 was used and subjected to the first test of decomposition ability in the case of varying the amount of the sample to measure the times required to decompose 50% and 90% of 20 ppm of acetaldehyde. The results are shown in Table 6 below.

TABLE 6

| | Amount of sample 2 (g) | Time required to decompose 20 ppm of acetaldehyde (minute) | |
|---|---|---|---|
| | | Time required to decompose 50% | Time required to decompose 90% |
| Sample 2 | 1 | 25 | 120 |
| Sample 15 | 30 | 5 | 20 |
| Sample 16 | 100 | 2.5 | 10 |
| Sample 17 | 500 | 1.5 | 5 |

It was found from Table 6 that if the amount of the photocatalyst material was increased, the decomposition ability was outstandingly improved. It was also found that if the amount of the photocatalyst was increased, this brought about an early rise in the development of the decomposition ability so that the time required to decompose 50% of acetaldehyde was shortened.

FOURTEENTH EMBODIMENT

FIG. 26 is a conceptual view showing an embodiment of a deodorizing apparatus according to the present invention. In FIG. 26, reference numeral 91 represents a deodorizing filter. A lamp 92 is disposed on the side wall side of the deodorizing filter 91. The deodorizing filter 91 and the lamp 92 are received in a deodorizing apparatus body 93 used as a casing.

The deodorizing filter 91 is prepared by forming a photocatalyst film mainly containing $WO_3$ microparticles having an average particle diameter of 0.05 to 0.1 μm on the surface of a base material, the surface being made permeable so as to carry out deodorization when air is allowed to flow. In short, the deodorizing filter 91 is allowed to be provided with a dust collecting function. Alternatively, a dust collecting filter may be disposed in a front stage of the passage of air of the deodorizing filter 91. As the photocatalyst material in this embodiment, those showing a decomposition ability of 90% or more in the first test of decomposition ability and a residual amount of 40% or less in the second test of decomposition ability were used.

The lamp 92 is used to irradiate light including visible rays to the deodorizing filter 91 to activate the photocatalyst film, and as the lamp 92, a fluorescent lamp, high-pressure mercury lamp, light-emitting diode or the like may be used. The deodorizing apparatus body 93 is provided with air blowing means, a power source and control means. Then, smelly gas is decomposed and deodorized by the photocatalyst film of the deodorizing filter 91 when it is allowed to pass through the deodorizing filter 91.

FIG. 27 is a graph showing the results of the photocatalyst effect measured in this embodiment. In FIG. 27, the abscissa is the time (min.) and the ordinate is the concentration (ppm) of acetaldehyde ($CH_3CHO$). This measurement was made with the intention of examining the decomposition of acetaldehyde, that is, a deodorizing effect. As to the condition of measurement, the deodorizing apparatus of FIG. 11 was received in a 0.2 m³ box filled with 500 ppm of acetaldehyde to drive the deodorizing apparatus, thereby measuring a variation in the concentration of acetaldehyde by a multi-gas monitor (trade name: 1302 type, manufactured by B & K company) while stirring the atmosphere in the box. The line a is obtained when these results are plotted. Also, for comparison, the lamp was changed to a bactericidal lamp which was a ultraviolet light source and a deodorizing filter (line b) formed of a photocatalyst film containing titanium oxide as its major component and a deodorizing filter (line c) formed of no photocatalyst film were used as the deodorizing filter to measure a change in the concentration of acetaldehyde in the same condition as above.

As is clear from FIG. 27, in this embodiment, the concentration of acetaldehyde was reduced to 20% in 30 minutes after the lamp was turned on. In the case of the titanium oxide photocatalyst (line b), to the contrary, the concentration of acetaldehyde was reduced by only 35% and in the case where no photocatalyst film was formed (line c), the concentration of acetaldehyde was hardly decreased in 30 minutes after the lamp was turned on. From the above fact, it was confirmed that the photocatalyst film containing $WO_3$ microparticles as its major component according to this embodiment had excellent effects on the decomposition of acetaldehyde when it was irradiated with visible light.

FIFTEENTH EMBODIMENT

Figure 28:
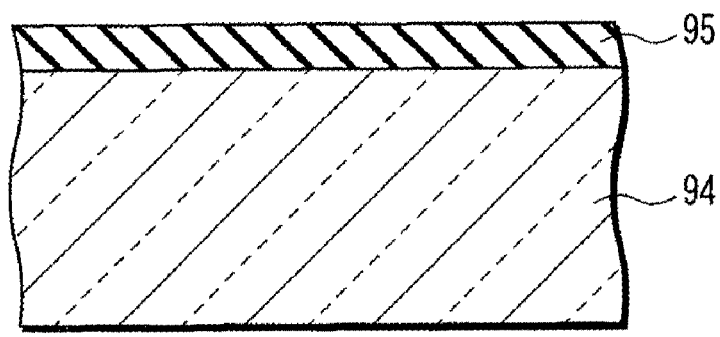
FIG. 28 shows an embodiment of another photocatalyst product according to this embodiment.

FIG. 28 is a conceptual enlarged sectional view of an essential part showing another embodiment of the photocatalyst product of the present invention. In FIG. 28, reference numeral 94 represents a base material made of soda lime glass and reference numeral 95 represents a photocatalyst film. The photocatalyst film 95 is primarily constituted of a tungsten oxide powder having an average particle diameter of 0.05 to 0.1 μm. The powders are bound with the base material 94 by a binder such as silica microparticles and formed on the base material 94 to form the photocatalyst film 95. As the tungsten oxide powder, those showing a decomposition ability of 90% or more in the first test of decomposition ability and a residual amount of 40% or less in the second test of decomposition ability were used.

When the photocatalyst film 94 is irradiated with light including visible rays having a wavelength of 400 nm or more, the tungsten oxide powder is photo-exited. Then, electrons excited to move into the conduction band from the valence band are reacted with oxygen in the air to form a super oxide and holes left in the valence band are reacted with water or the like to make an OH group. The materials produced in this manner give rise to an oxidation reaction with organic materials attached to the surface of the photocatalyst film. The organic materials are oxidized and decomposed to thereby obtain anti-contamination, deodorizing and bactericidal effects.

Also, as to the bactericidal effect, the photocatalyst has such an effect that bacteria adsorbed to the surface of the photocatalyst is limited in proliferation by the oxidizing power of the tungsten oxide powder. It has been confirmed that this effect is almost proportional to the decomposition rate of dyes. Meanwhile, the bactericidal force is more improved by combining the irradiation with ultraviolet rays having a wavelength of 200 to 400 nm. Among these wavelengths, ultraviolet rays having a wavelength close to 250 nm produce the largest effect. Moreover, ultraviolet rays having a wavelength close to 350 nm are reduced in bactericidal ability to 1/1000 of that of ultraviolet rays having a wavelength close to 250 nm. Moreover, the bactericidal effect of ultraviolet rays having a wavelength close to 350 nm is increased in combination with the photocatalyst effect. As a result, because the rate of adsorption to the surface of the photocatalyst determines the bactericidal rate, a large bactericidal action is not expected and it is therefore preferable to use ultraviolet rays having a wavelength close to 250 nm.

Figure 29:
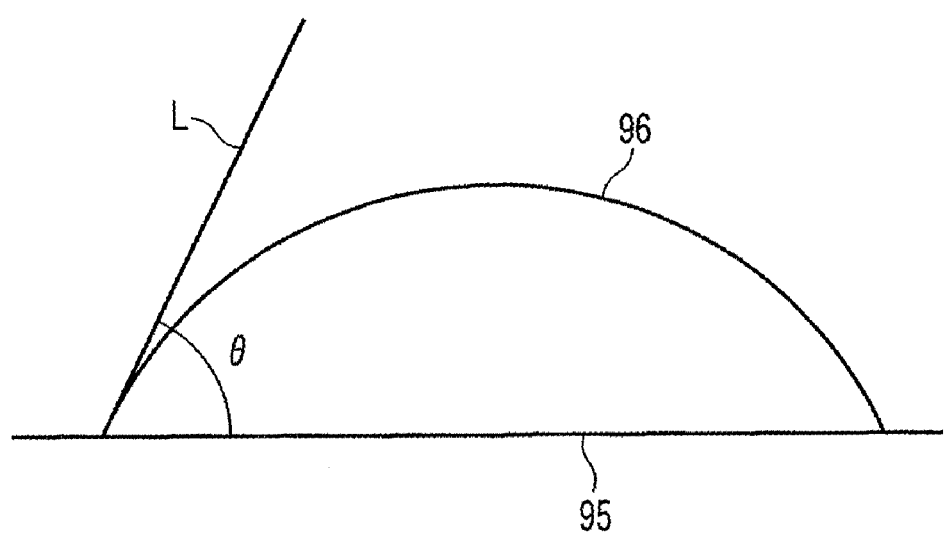
FIG. 29 shows one example of hydrophilic characteristics of the photocatalyst product according to this embodiment.

FIG. 29 is a conceptual view for explaining the hydrophilic ability of the photocatalyst body in this embodiment. Reference numeral 96 is a water droplet dripped on the photocatalyst film 95. It is understood that when the contact angle θ of the photocatalyst film 95 with the water droplet 96 is 60° or less, the photocatalyst film 95 is hydrophilic. In FIG. 29, L is a tangent line.

From the above results, it is found that the photocatalyst product in this embodiment may be applied to bactericidal uses and also to uses which need a photocatalyst effect not only on gas components but also on an aqueous solution because it has hydrophilic ability.

It is to be noted that this invention is not limited to the above embodiments exactly as they stand and may be embodied by modifying the structural elements without departing from the spirit in the practical stage. Also, various inventions can be made by proper combinations of plural structural elements disclosed in the above embodiments. For example, several structural elements may be deleted from all the structural elements shown in the embodiments. Moreover, the structural elements in different embodiments may be combined.

What is claimed is:

1. A photocatalyst composition comprising 50% by mass or more of a photocatalyst material comprising, as its major component, a tungsten oxide powder having an average grain diameter of 0.5 μm or less and mainly containing monoclinic crystals, excited by a light source which emits light having a wavelength of 430 to 500 nm, with a peak wavelength of 460 nm+10 nm, wherein the photocatalyst material has a decomposition ability of 50% or more which is determined by the following equation based on the following test:

[Test for decomposition ability]

1 g of a tungsten oxide powder and 20 ppm of acetaldehyde (amount A) are poured into a 3-liter glass container, and acetaldehyde (amount B) is measured after light having a peak wavelength of 460 nm+10 nm is irradiated to the mixture for 2 hours to measure the decomposition ability (%):

Decomposition ability (%)=[(acetaldehyde amount $A$−acetaldehyde amount $B$)/acetaldehyde amount $A$]×100.

2. The photocatalyst composition according to claim 1, wherein the light source is a light-emitting diode using a blue light-emitting semiconductor element.

3. The photocatalyst composition according to claim 1, wherein the light source is sunlight.

4. The photocatalyst composition according to claim 1, wherein the light source is a fluorescent lamp.

5. The photocatalyst composition according to claim 1, wherein dose of light having a wavelength of 430 to 500 nm is 1 mW/cm$^2$ or more.

6. The photocatalyst composition according to claim 1, wherein the decomposition ability is 90% or more and 100% or less.

7. The photocatalyst composition according to claim 1, comprising a monoclinic system as its major phase.

8. The photocatalyst composition according to claim 1, comprising a titanium oxide powder in an amount less than 50% by mass.

9. A photocatalyst product comprising the photocatalyst composition according to claim 1.

10. The photocatalyst product according to claim 9, having a catalyst effect on at least one of an organic material, NO$_x$ and SO$_x$.

11. The photocatalyst product according to claim 9 or 10, wherein the photocatalyst composition is bound with a surface of a base substrate by a binder.

12. A photocatalyst composition comprising 50% by mass or more of a photocatalyst material comprising, as its major component, a tungsten oxide microparticle having an average grain diameter of 0.5 μm or less and mainly containing monoclinic crystals, excited by irradiation with blue light, wherein the photocatalyst material has a residual rate of acetaldehyde of 50% or less determined by the following equation based on the following test:

[Test for decomposition ability]

1 g of a tungsten oxide powder and 10 ppm of acetaldehyde are poured into a 3-liter glass container, and acetaldehyde is measured after the blue light having a peak wavelength of 460 nm+10 nm is irradiated to the mixture for 30 minutes to measure the residual rate of acetaldehyde (%):

Residual rate (%)=[(10 ppm acetaldehyde amount remained after 30 minutes)/10 ppm]×100.

13. The photocatalyst composition according to claim 12, wherein a light source which emits blue light is a GaN system light-emitting diode having a light-emitting peak in the vicinity of 470 nm.

14. The photocatalyst composition according to claim 12, comprising a monoclinic system as its major phase.

15. The photocatalyst composition according to claim 12, comprising a titanium oxide powder in an amount less than 50% by mass.

16. A photocatalyst product comprising the photocatalyst composition according to claim 12.

17. The photocatalyst product according to claim 16, having a catalyst effect on at least one of an organic material, NO$_x$ and SO$_x$.

18. The photocatalyst product according to claim 16 or 17, wherein the photocatalyst composition is bound with a surface of a base substrate by a binder.

* * * * *